United States Patent
Stigall et al.

(10) Patent No.: US 12,232,908 B2
(45) Date of Patent: Feb. 25, 2025

(54) LINED VARIABLE BRAIDED DIFFERENTIAL DUROMETER MULTI-LUMEN SHAFT WITH A CROSS-SHAPED INNER PROFILE

(71) Applicant: PHILIPS IMAGE GUIDED THERAPY CORPORATION, San Diego, CA (US)

(72) Inventors: Jeremy Stigall, Carlsbad, CA (US); Princeton Saroha, Ladera Ranch, CA (US); Maritess Minas, San Diego, CA (US)

(73) Assignee: Philips Image Guided Therapy Corporation, San Diego, CA (US)

( * ) Notice: Subject to any disclaimer, the term of this patent is extended or adjusted under 35 U.S.C. 154(b) by 0 days.

(21) Appl. No.: 18/200,353

(22) Filed: May 22, 2023

(65) Prior Publication Data
US 2023/0293148 A1    Sep. 21, 2023

Related U.S. Application Data

(63) Continuation of application No. 16/336,511, filed as application No. PCT/EP2017/074151 on Sep. 25, 2017, now Pat. No. 11,653,895.

(60) Provisional application No. 62/401,464, filed on Sep. 29, 2016.

(51) Int. Cl.
*A61B 8/00* (2006.01)
*A61B 8/12* (2006.01)

(52) U.S. Cl.
CPC .............. *A61B 8/12* (2013.01); *A61B 8/445* (2013.01)

(58) Field of Classification Search
None
See application file for complete search history.

(56) References Cited

U.S. PATENT DOCUMENTS

| | | | |
|---|---|---|---|
| 4,846,791 A | 7/1989 | Hattler | |
| 5,395,328 A | 3/1995 | Ockuly | |
| 6,500,167 B1* | 12/2002 | Webster, Jr. | A61M 25/0136 604/95.04 |
| 2004/0039332 A1 | 2/2004 | Kantor | |
| 2008/0281293 A1* | 11/2008 | Peh | A61B 1/00082 604/523 |
| 2010/0179426 A1* | 7/2010 | Davies | A61B 8/4483 600/439 |

(Continued)

FOREIGN PATENT DOCUMENTS

| | | |
|---|---|---|
| JP | H08136823 A | 5/1996 |
| JP | H09000525 A | 1/1997 |

*Primary Examiner* — Amal Aly Farag

(57) ABSTRACT

An imaging catheter is provided. In one embodiment, the imaging catheter includes a flexible elongate member that includes a proximal portion formed of a first material embedded with a first braid with a first braid pitch; a distal portion formed of a second material embedded with a second braid with a second braid pitch, wherein the second material is a lower durometer than the first material and wherein the second braid pitch is a higher per inch count than the first braid pitch such that the distal portion is more flexible than the proximal portion; a primary lumen extending between the proximal portion and the distal portion; and a plurality of secondary lumens extending between the proximal portion and the distal portion; and an imaging component coupled to the distal portion of the flexible elongate member.

11 Claims, 23 Drawing Sheets

(56) References Cited

U.S. PATENT DOCUMENTS

2012/0108979 A1    5/2012  Franklin
2013/0345679 A1*  12/2013  Garon .................. A61M 27/00
                                                    604/541
2014/0018732 A1*   1/2014  Bagaoisan ........ A61M 25/0136
                                                    604/95.04
2014/0336572 A1   11/2014  Heisel

* cited by examiner

LINED VARIABLE BRAIDED DIFFERENTIAL DUROMETER MULTI-LUMEN SHAFT WITH A CROSS-SHAPED INNER PROFILE

CROSS-REFERENCE TO RELATED APPLICATIONS

This application is a continuation of application Ser. No. 16/336,511, filed Mar. 26, 2019, now U.S. Pat. No. 11,653,895, which is the U.S. National Phase application under 35 U.S.C. § 371 of International Application No. PCT/EP2017/074151, filed on Sep. 25, 2017, which claims the benefit of Provisional Application Ser. No. 62/401,464, filed Sep. 29, 2016. These applications are hereby incorporated by reference herein.

TECHNICAL FIELD

The present disclosure relates generally to ultrasound catheters, in particular, to an intracardiac echocardiography (ICE) catheter shaft structured to improve flexibility, kink resistance, and steerability and to facilitate alignment during manufacturing.

BACKGROUND

Diagnostic and therapeutic ultrasound catheters have been designed for use inside many areas of the human body. In the cardiovascular system, two common diagnostic ultrasound methods are intravascular ultrasound (IVUS) and intracardiac echocardiography (ICE). Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

IVUS catheters are typically used in the large and small blood vessels (arteries or veins) of the body, and are almost always delivered over a guidewire having a flexible tip. ICE catheters are usually used to image chambers of the heart and surrounding structures, for example, to guide and facilitate medical procedures, such as transseptal lumen punctures, left atrial appendage closures, atrial fibrillation ablation, and valve repairs. Commercially-available ICE catheters are not designed to be delivered over a guidewire, but instead have distal ends which can be articulated by a steering mechanism located in a handle at the proximal end of the catheter. For example, an ICE catheter may be inserted through the femoral or jugular artery when accessing the anatomy, and steered in the heart to acquire images necessary to the safety of the medical procedures.

One type of ICE catheter (EP Medsystems ViewFlex™ Intracardiac Ultrasound Deflectable catheter) has a distal articulation in a single plane (both directions), operated by a single wheel that rotates about the lengthwise axis of the handle. The wheel is turned to a specific position for the desired catheter shape, staying in place due to the inherent friction on the wheel mechanism. The catheter is torquable, and can be rotated with the handle to facilitate steering in a second plane. The motions required to simultaneously torque and rotate the catheter often require two-handed operation.

Another type of ICE catheter (Siemens/ACUSON Acu-Nav™ Ultrasound Catheter) has an additional steering plane, and each steering plane is utilized by turning one of two corresponding wheels on the handle. These wheels rotate about the lengthwise axis of the handle. A third wheel, which also rotates about the lengthwise axis of the handle, is a locking mechanism for freezing each of the two steering wheels in its respective orientation. The entire catheter need not be torqued. The two steering planes allow a large combination of possible catheter configurations.

ICE catheters commonly provide steering through pullwires secured to the distal portions of the catheters near the tip assemblies. The pullwires are also referred to as steering lines. The pullwires extend through the bodies of the catheters and are coupled to control wheels at handles of the catheters located at the proximal end of catheters. For example, a pair of pullwires may provide steering in a left-right plane and another pair of pullwires may provide steering in an anterior-posterior plane. Thus, the maneuvering or turning of a control wheel in turn actuates a corresponding pullwire to deflect the distal portion of a catheter in a corresponding direction.

An ICE catheter typically includes an ultrasound imaging core that generates and receives acoustic energy. The imaging core may include a linear array of transducer elements or transducer elements arranged in any suitable configuration. The imaging core is encased in a tip member located at a furthest distal tip of the catheter. The tip member is covered with acoustic adhesive materials. An electrical cable is soldered to the imaging core and extends through the core of the body of the catheter. The electrical cable may carry control signals and echo signals to facilitate imaging of the heart anatomy.

Current commercial ICE catheters are manufactured as one time use disposable devices. However, customers commonly employ third party vendors to reprocess the used devices for additional procedures up to a certain limit (e.g., about 6). For examples, the catheter shaft can be adapted as the primary shaft and actuating body for any steerable disposable, including other types of diagnostic catheters, such as optical coherence tomography (OCT), electrophysiology (EP) mapping, and pressure sensing catheters, delivery catheters, guide sheathes, and therapeutic devices (e.g., ablation catheters).

SUMMARY

The invention provides devices, systems, and related methods that overcome the limitations associated with existing designs and provide durable and flexible catheter shafts.

Embodiments of the present disclosure provide a catheter with a lined variable braided catheter shaft. The body or the wall of the catheter shaft includes a high differential durometer between a distal segment and a proximal segment, creating a sharp transition. The body or the wall of the catheter shaft includes an embedded variable braided reinforcement layer. For example, the braided layer includes braids with a higher per inch count (PIC) at the distal segment than at the proximal segment. In addition, a portion of the braided layer around the sharp transition includes braids with varying PIC to provide a smooth transition from the high PIC at the distal segment to the low PIC at the proximal segment. The catheter shaft includes a central lumen with a cross-shaped cross-sectional profile that can facilitate alignment of pullwire lumens during manufacturing.

In one embodiment, an imaging catheter is provided. The imaging catheter includes a flexible elongate member that includes a proximal portion comprising a first material embedded with a first braid with a first braid pitch; a distal portion comprising a second material embedded with a second braid with a second braid pitch, wherein the second material is a lower durometer than the first material and wherein the second braid pitch includes a higher per inch count than the first braid pitch such that the distal portion is more flexible than the proximal portion; a primary lumen extending at least partially through the proximal portion and the distal portion; and a plurality of secondary lumens extending at least partially through the proximal portion and the distal portion; and an imaging component coupled to the distal portion of the flexible elongate member.

In some embodiments, the first material comprises a polyether block amide of durometer 72D. In some embodiments, the second material comprises a polyether block amide of durometer 35D or 45D. In some embodiments, the first braid and the second braid are constructed from flat wires. In some embodiments, the flat wires are composed of steel. In some embodiments, the first braid pitch includes a first per inch count, and wherein the second braid pitch includes a second per inch count that is about twice the first per inch count. In some embodiments, the flexible elongate member includes a third braid embedded within the first material and the second material across a transition between the proximal portion and the distal portion, and wherein the third braid includes variable braid pitches that transition between a first per inch count of the first braid pitch and a second per inch count of the second braid pitch. In some embodiments, the primary lumen includes a cross-shaped cross-section. In some embodiments, the plurality of secondary lumens are positioned relative to the primary lumen between arms of the cross-shaped cross-section. In some embodiments, the imaging catheter further includes a communication cable coupled to the imaging component and extending through the primary lumen. In some embodiments, the imaging catheter further includes a plurality of steering lines coupled to the distal portion of the flexible elongate member and extending through the plurality of secondary lumens. In some embodiments, the imaging component is an ultrasound transducer array. In some embodiments, the distal portion is deflectable up to a radius curvature of about 14 millimeters (mm).

In one embodiment, a method of manufacturing an imaging catheter is provided. The method includes forming a proximal portion of a flexible elongate member with a first material embedded with a first braid with a first braid pitch, wherein the proximal portion includes a first primary lumen and a first plurality of secondary lumens; forming a distal portion of the flexible elongate member with a second material embedded with a second braid with a second braid pitch, wherein the second material is a lower durometer than the first material and wherein the second braid pitch includes a higher per inch count than the first braid pitch such that the distal portion is more flexible than the proximal portion; and coupling an imaging component to the distal portion of the flexible elongate member.

In some embodiments, the first material comprises a polyether block amide of durometer 72D. In some embodiments, the second material comprises a polyether block amide of durometer 35D or 45D. In some embodiments, the first braid and the second braid are constructed from stainless steel flat wires. In some embodiments, the first braid pitch includes a first per inch count, and wherein the second braid pitch includes a second per inch count that is about twice the first per inch count. In some embodiments, the method further includes forming a third braid within the first material and the second material across a transition between the proximal portion and the distal portion, and wherein the third braid includes variable braid pitches that transition between a first per inch count of the first braid pitch and a second per inch count of the second braid pitch. In some embodiments, the forming the proximal portion includes forming the proximal portion to define a cross-shaped cross section for the first primary lumen and to position the first plurality of secondary lumens relative to arms of the cross-shaped cross section. In some embodiments, the forming the distal portion includes forming the distal portion to define a second primary lumen in communication with the first primary lumen and to define a second plurality of secondary lumens in communication with the first plurality of secondary lumens. In some embodiments, the method of claim further includes coupling a communication cable to the imaging component; and extending the communication cable through the second primary lumen of the distal portion and the first primary lumen of the proximal portion. In some embodiments, the method further includes coupling a plurality of steering lines to the distal portion; and extending the plurality of steering lines through the second plurality of secondary lumens of the distal portion and the first plurality of secondary lumens of the proximal portion. In some embodiments, the imaging component is an ultrasound transducer array.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
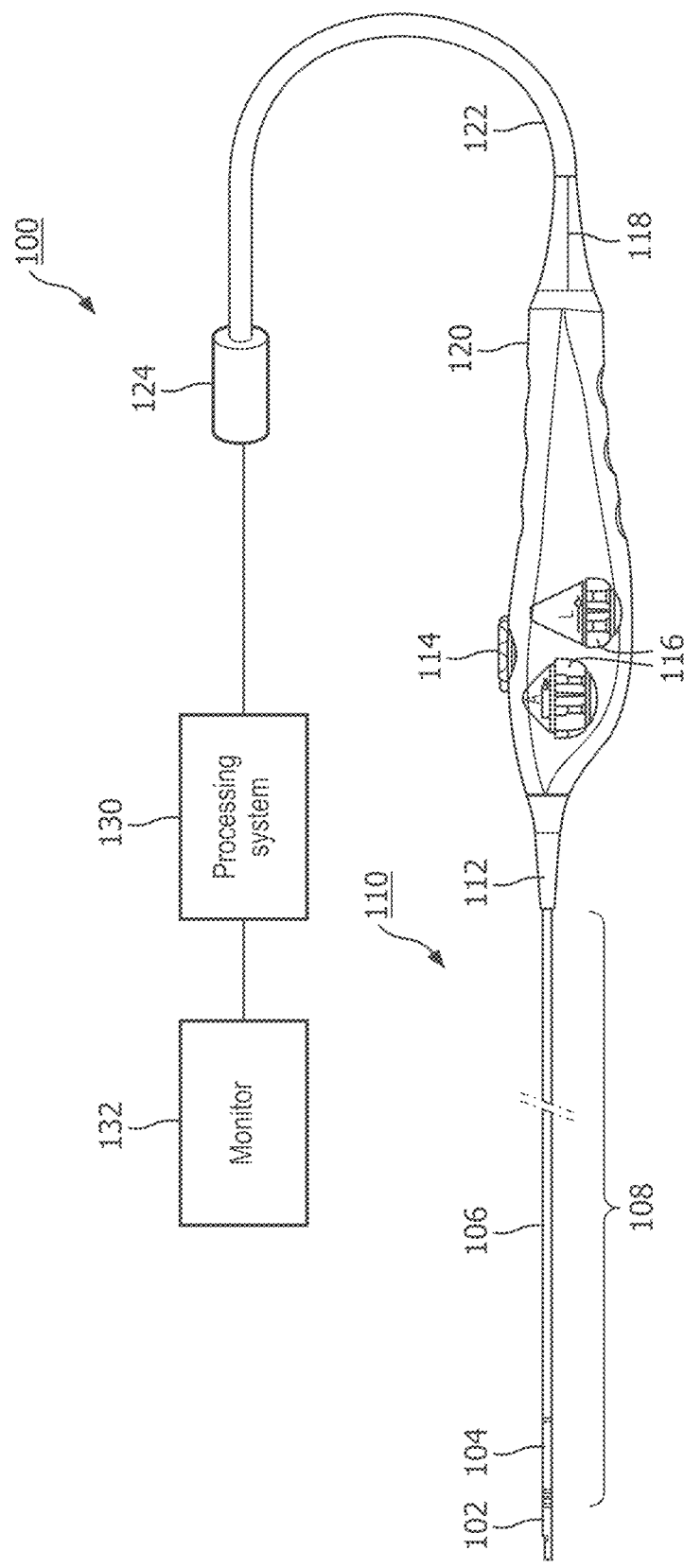
FIG. 1 is a schematic diagram of an ICE imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ICE system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ICE imaging system 100 according to embodiments of the present disclosure. The system 100 may include an ICE device 110, a connector 124, a control and processing system 130, such as a console and/or a computer, and a monitor 132. The ICE device 110 includes a tip assembly 102, a flexible elongate member 108, and a handle 120. The flexible elongate member 108 includes a distal portion 104 and a proximal portion 106. The distal end of the distal portion 104 is attached to the tip assembly 102. The proximal end of the proximal portion 106 is attached to the handle 120 for example, by a resilient strain reliever 112, for manipulation of the ICE device 110 and manual control of the ICE device 110. The tip assembly 102 can include an imaging core with ultrasound transducer elements and associated circuitry. The handle 120 can include actuators 116, a clutch 114, and other steering control components for steering the ICE device 110, such as deflecting the tip assembly 102 and the distal portion 104, as described in greater details herein.

The handle 120 is connected to the connector 124 via another strain reliever 118 and an electrical cable 122. The connector 124 may be configured in any suitable configurations to interconnect with the processing system 130 and the monitor 132 for processing, storing, analyzing, manipulating, and displaying data obtained from signals generated by the imaging core at the tip assembly 102. The processing system 130 can include one or more processors, memory, one or more input devices, such as keyboards and any suitable command control interface device. The processing system 130 can be operable to facilitate the features of the ICE imaging system 100 described herein. For example, the processor can execute computer readable instructions stored on the non-transitory tangible computer readable medium. The monitor 132 can be any suitable display device, such as liquid-crystal display (LCD) panel or the like.

In operation, a physician or a clinician advances the flexible elongate member 108 into a vessel within a heart anatomy. The physician or clinician can steer the flexible elongate member 108 to a position near the area of interest to be imaged by controlling the actuators 116 and the clutch 114 on the handle 120. For example, one actuator 116 may deflect the tip assembly 102 and the distal portion 104 in a left-right plane and the other actuator 116 may deflect the tip assembly 102 and the distal portion 104 in an anterior-posterior plane, as discussed in greater details herein. The clutch 114 provides a locking mechanism to lock the positions of the actuators 116 and in turn the deflection of the flexible elongate member while imaging the area of interest.

The imaging process may include activating the ultrasound transducer elements on the tip assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the processing system 130 where the ultrasound image is reconstructed and displayed on the monitor 132. In some embodiments, the processing system 130 can control the activation of the ultrasound transducer elements and the repletion of the echo signals. In some embodiments, the processing system 130 and the monitor 132 may be part of the same system.

The system 100 may be utilized in a variety of applications such as transseptal lumen punctures, left atrial appendage closures, atrial fibrillation ablation, and valve repairs and can be used to image vessels and structures within a living body. Although the system 100 is described in the context of ICE catheterization procedures, the system 100 is suitable for use with any catheterization procedure. In addition, the tip assembly 102 may include any suitable physiological sensor or component for diagnostic, treatment, and/or therapy.

Figure 2:
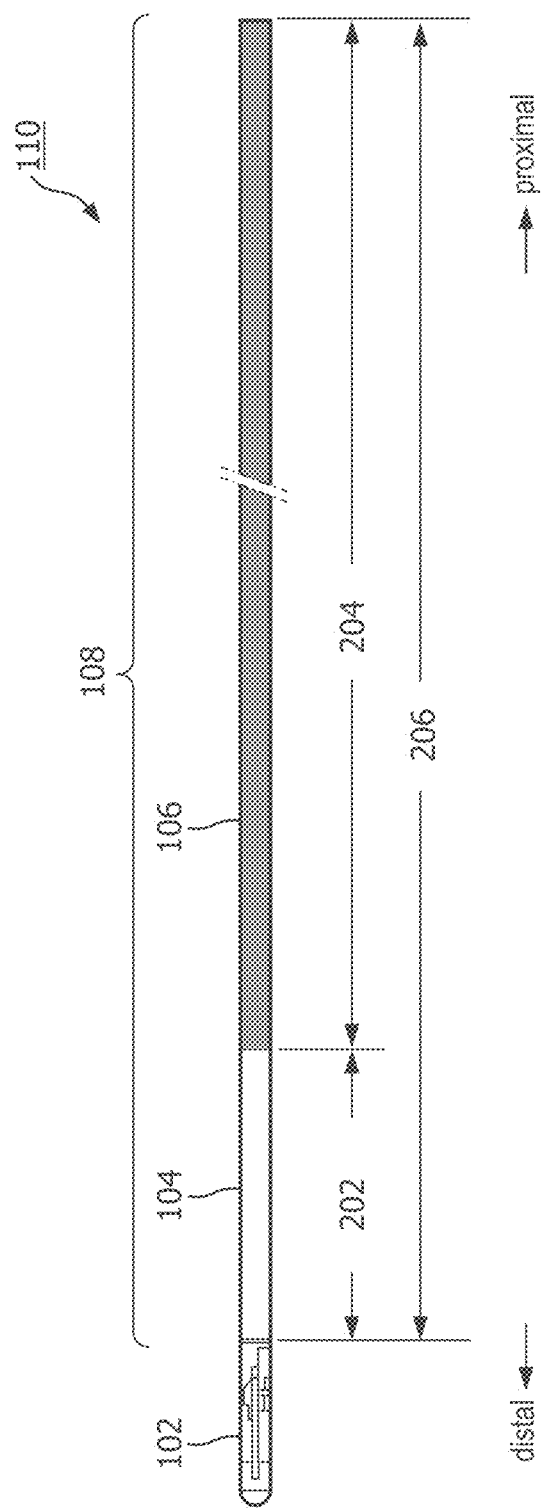
FIG. 2 is a schematic diagram of a portion of an ICE device according to embodiments of the present disclosure.

FIG. 2 is a schematic diagram of a portion of the ICE device 110 according to embodiments of the present disclosure. The tip assembly 102 and the flexible elongate member 108 are shaped and sized for insertion into vessels of a patient body. The flexible elongate member 108 can be composed of any suitable material, such as polyether block amides. Polyether block amides are commonly manufactured under the tradename Pebax®. The distal portion 104 and the proximal portion 106 are tubular in shape and may include a primary lumen and one or more pullwire lumens extending longitudinally along the flexible elongate member 108. The primary lumen is sized and shaped to accommodate an electrical cable interconnecting the tip assembly 102 and the connector 124 for transferring echo signals obtained from the transducer elements. In some embodiments, the primary lumen can be shaped and sized to accommodate other components for diagnostic and/or therapy procedures. The pullwire lumens are sized and shaped to accommodate pullwires, for example, extending from the distal portion 104 to the handle 120. The pullwires may be coupled to the actuators 116 and the clutch 114 such that the flexible elongate member 108 and the tip assembly 102 are deflectable based on actuations of the actuators 116 and the clutch 114. In an embodiment, the primary lumen is shaped to facilitate alignment of the pullwire lumens. In addition, the tubular body of the flexible elongate member 108 may include a lined variable braided reinforcement layer configured to provide flexibility and kink resistance. The arrangements and configurations of the pullwires, the primary lumen, the pullwire lumens, the tip assembly 102, and the lined variable braided reinforcement layer are described in greater details herein. Dimensions of the flexible elongate member 108 can vary in different embodiments. In some embodiments, the flexible elongate member 108 can be a catheter having an outer diameter between about 8 and about 12 French (Fr) and can have a total length 206 between about 80 centimeters (cm) to about 120 cm, where the proximal portion 106 can have a length 204 between about 70 cm to about 118 cm and the distal portion 104 can have a length 202 between about 2 cm to about 10 cm.

Figure 3:
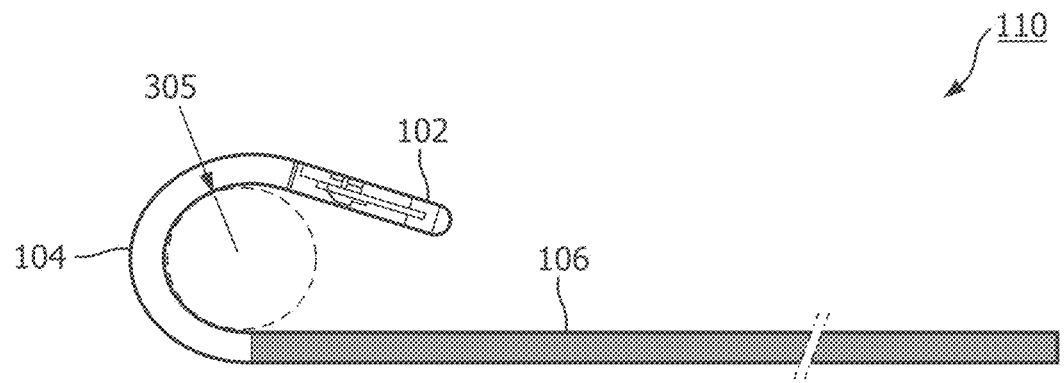
FIG. 3 is a schematic diagram of a portion of an ICE device under deflection according to embodiments of the present disclosure.

FIG. 3 is a schematic diagram of a portion of the ICE device 110 under deflection according to embodiments of the present disclosure. For example, the flexible elongate member 108 shown in FIG. 2 is referred to as a neutral position. In FIG. 3, the tip assembly 102 and the distal portion 104 of the flexible elongate member 108 are deflected from the neutral position. In an embodiment, the distal portion 104 may be deflected up to a bend radius 305 of about 27 millimeters (mm) to about 28 mm.

Figure 4:
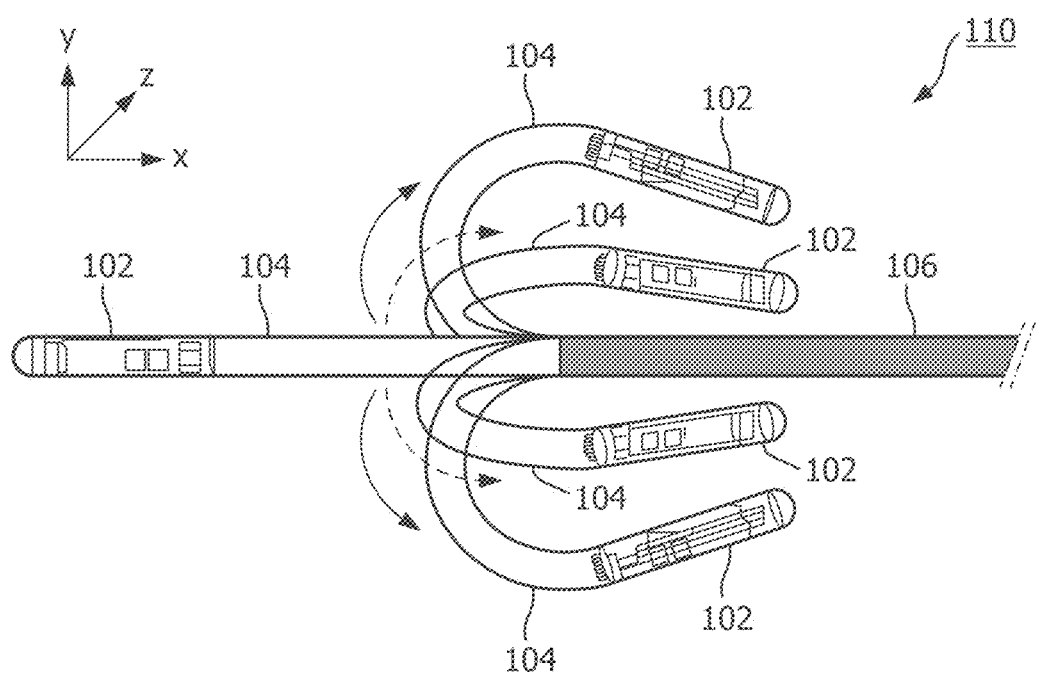
FIG. 4 is a schematic diagram illustrating deflections planes of an ICE device according to embodiments of the present disclosure.

FIG. 4 is a schematic diagram illustrating deflections planes of the ICE device 110 according to embodiments of the present disclosure. As shown, the tip assembly 102 and the distal portion 104 can be deflected along a first plane as shown by the solid arrows and a second plane as shown by the dotted arrows. In FIG. 3, the first plane is represented by an x-y plane and the second plane is represented by an x-z plane. For example, the x-y plane may correspond to a left-right plane and the x-z plane may correspond to an anterior-posterior plane for imaging the heart anatomy.

Figure 5:
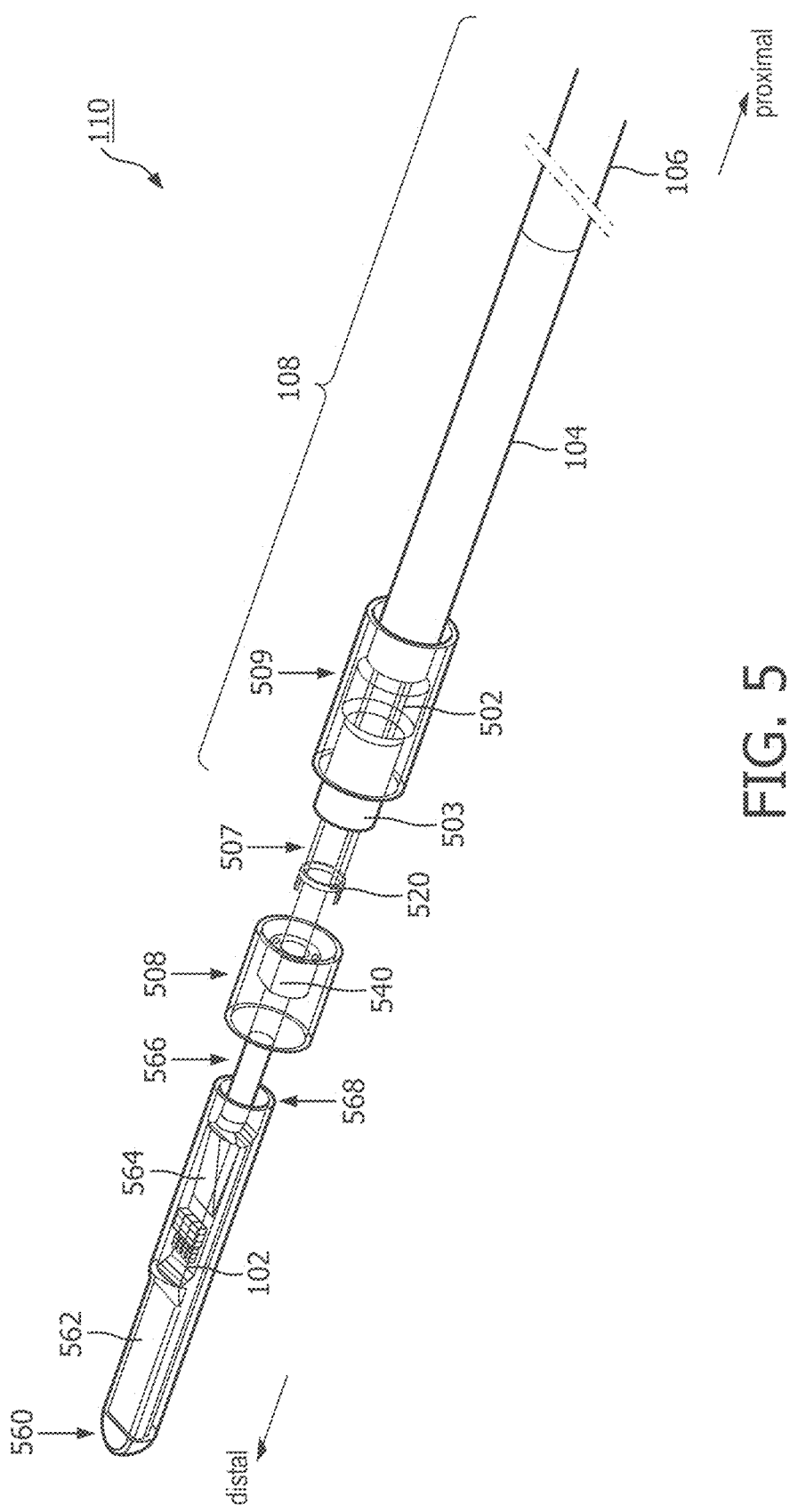
FIG. 5 is a schematic diagram illustrating an interconnection within an ICE device between a tip assembly and a flexible elongate member according to embodiments of the present disclosure.

FIG. 5 is a schematic diagram illustrating an interconnection within the ICE device 110 between the tip assembly 102 and the flexible elongate member 108 according to embodiments of the present disclosure. As shown, the interconnection between the tip assembly 102 and the distal portion 104 of the flexible elongate member 108 includes a crown element 520 and a sleeve element 540. The crown element 520 is coupled to the distal end of the distal portion 104. The sleeve element 540 is coupled to the crown element 520 and the proximal end of the tip assembly 102. The tip assembly 102 includes an imaging core 562 encased in a tip member 560. For example, the imaging core 562 is a planar element. The tip assembly 102 can include an alignment portion (not shown) shaped to facilitate alignment during manufacturing, as described in greater detail herein. The imaging core 562 is connected to an electrical cable 566 via an electrical interconnection 564. The electrical cable 566 extends longitudinally along the flexible elongate member 108. The crown element 520 and the sleeve element 540 are fitted around the electrical cable 566.

The electrical cable 566 may include one or more cables and/or one or more wires formed into cables. In certain embodiments, the one or more cables or wires are encased or surrounded at least partially along their length with a heat shrink tubing. In some instances, the one or more cables may be split or arranged into separate heat shrink tubing. The heat shrink tubing is typically a polymeric material. An ideal polymeric material is polyethylene terephthalate (PET). The heat shrink tubing material may be manufactured using an extrusion process. Ideally the tubing is manufactured such that the expanded ID clears width of the cables to be threaded there through, and the shrunked ID is such that it forms a interference fit with the cables threaded there through.

Figure 6A:
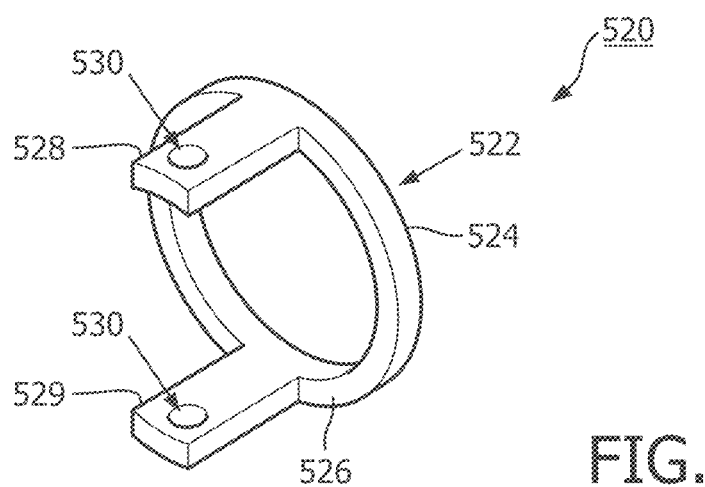
FIG. 6A is a perspective view of a crown element according to embodiments of the present disclosure.
Figure 6B:
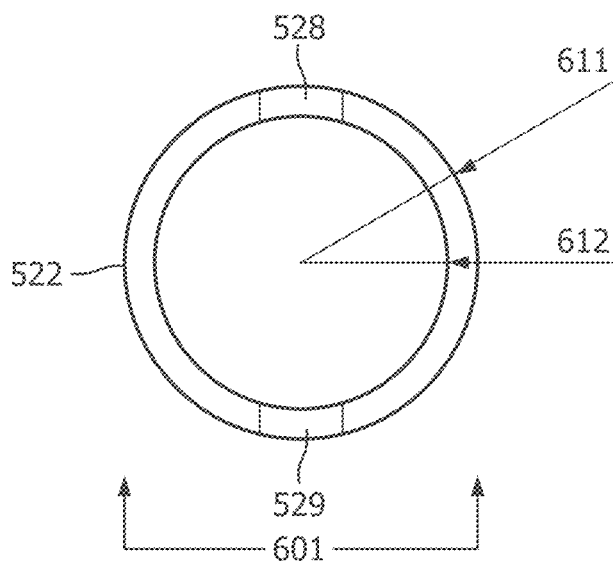
FIG. 6B is a bottom view of a crown element according to embodiments of the present disclosure.
Figure 7:
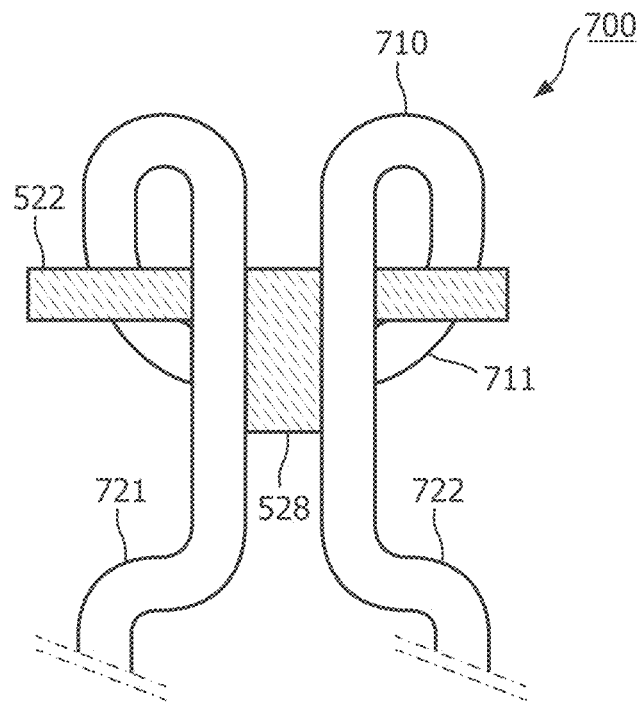
FIG. 7 is a side view of a crown element with a pullwire in position according to embodiments of the present disclosure.
Figure 8A:
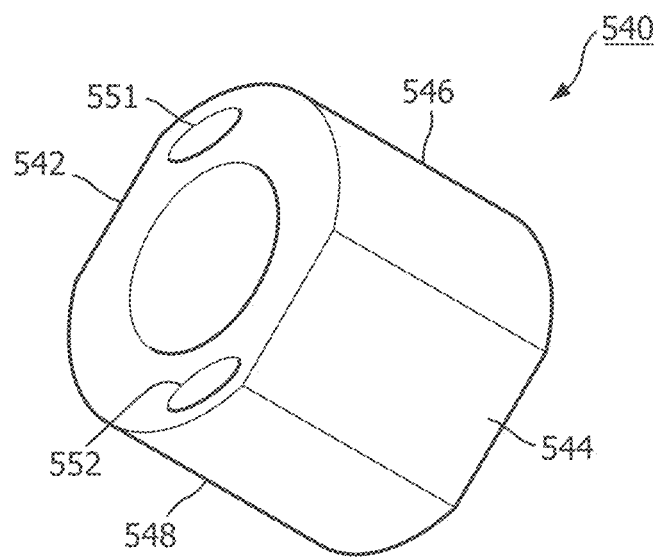
FIG. 8A is a perspective view of a sleeve element according to embodiments of the present disclosure.
Figure 26:
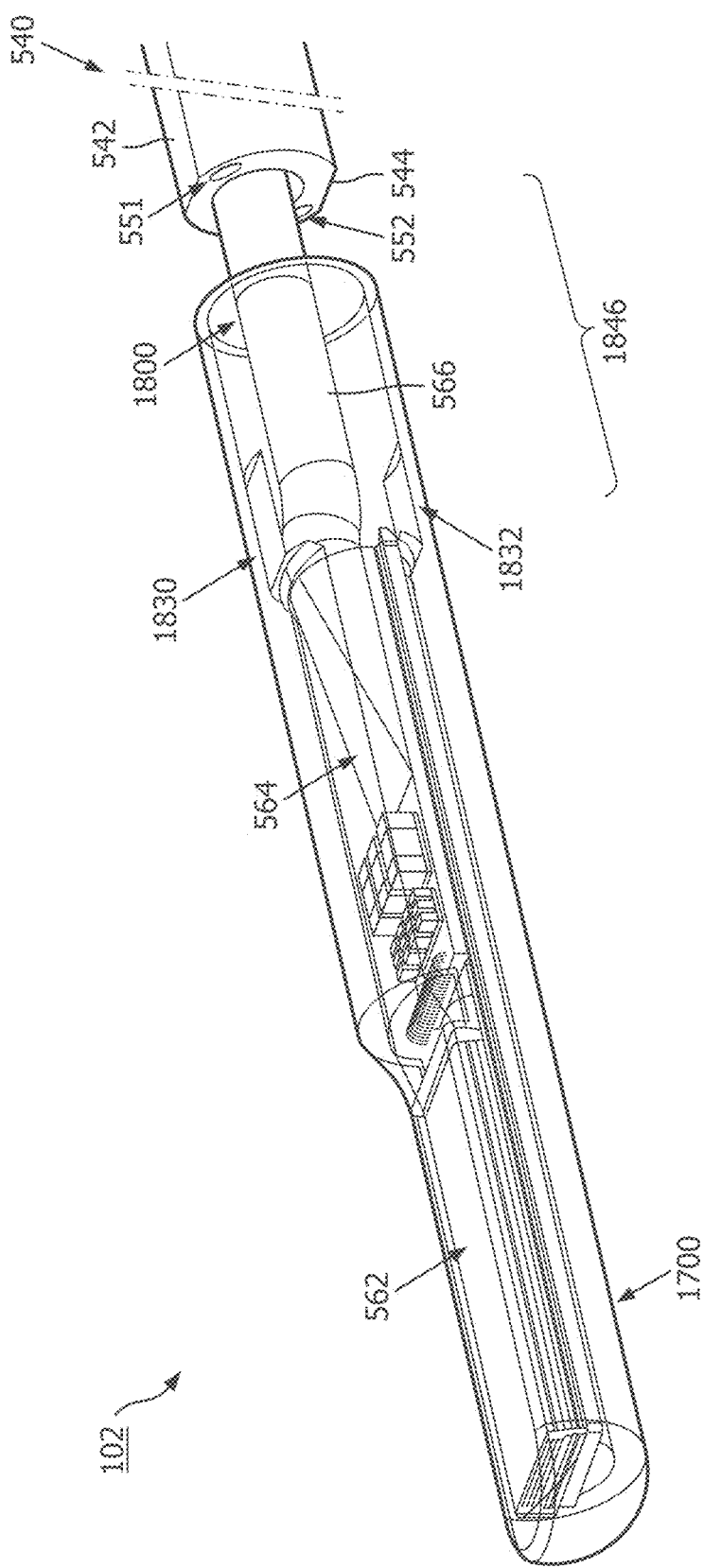
FIG. 26 is a perspective view of a tip assembly and a sleeve element positioned for coupling according to embodiments of the present disclosure.

A more detailed view of the crown element 520 is illustrated in FIG. 6A and dimensions of the crown element 520 are illustrated in FIGS. 6B and C. The crown element 520 functions as an anchor for pullwires 507 such that the tip assembly 102 and the distal portion 104 may be deflectable upon actuations of the pullwires 507 in the proximal direction as shown in FIGS. 3 and 4 and described in greater detail herein. The anchoring of the pullwires 507 to the crown element 520 is illustrated in FIG. 7. The sleeve element 540 functions as an alignment agent to align the crown element 520 and the pullwires 507 such that the deflection may provide predictable or predetermined articulation views as described in greater detail herein. A more detailed view of the sleeve element 540 is illustrated in FIG. 8A. The alignment between the sleeve element 540 and the tip assembly 102 is illustrated in FIG. 26.

In an embodiment, the flexible elongate member 108 may include a lined variable braided enforcement layer to provide flexibility and kink resistance as described in greater detail herein. In such an embodiment, the interconnection further includes a braid containment 502 positioned between an anchoring segment 503 and the distal end of the flexible elongate member 108. The braid containment 502 may be composed of material such as polyethylene terephthalate (PET) or any suitable material. The anchoring segment 503 can be composed of similar material as the flexible elongate member 108. The braid containment 502 functions as a termination for the braided reinforcement layer. The braid containment 502 encases the termination of the materials (e.g., stainless steel wires) of the braided reinforcement layer to prevent exposure of the materials outside of the ICE device 110. The structure of the flexible elongate member 108 and the braided reinforcement layer are described in greater detail herein. The anchoring segment 503 couples the braid containment 502 to the crown element 520 and the sleeve element 540 to allow for thermal reflow when bonding the components at the interconnection.

The interconnection may further include support members 508 and 509, which are thin sleeves, to provide protection over connections of different components. The support members 508 and 509 may be composed of any suitable polymeric material. As shown, the support member 508 is positioned over the connections among the sleeve element 540, the tip assembly 102, the crown element 520, and the anchoring segment 503. The support member 509 is positioned over the connections among the braid containment 502, the anchoring segment 503, and the distal portion 104 of the flexible elongate member 108.

Figure 6C:
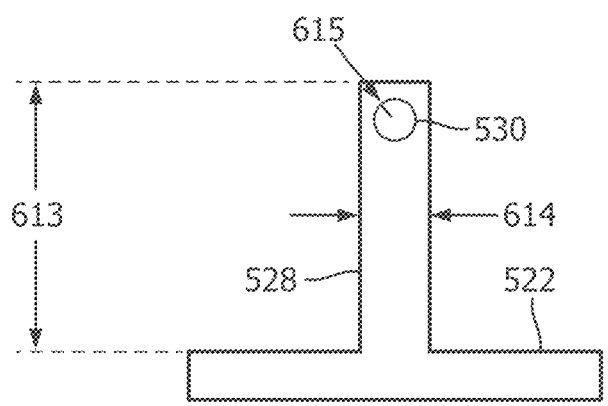
FIG. 6C is a side view of a crown element according to embodiments of the present disclosure.

FIG. 6A is a perspective view of the crown element 520 according to embodiments of the present disclosure. FIG. 6B is a bottom view of the crown element 520 according to embodiments of the present disclosure. FIG. 6C is a side view of the crown element 520 taken along the line 601 of FIG. 6B according to embodiments of the present disclosure. The crown element 520 includes an annular ring 522 and support legs or posts 528 and 529. The crown element 520 is composed of a material dissimilar or incompatible with the material of the flexible elongate member 108. For example, the crown element 520 is composed of a thermoset material such as metal or plastic polymer. The annular ring 522 includes a top surface 524 and a bottom surface 526. The posts 528 and 529 are positioned about radially opposite of each other on the annular ring 522 and extend about perpendicularly from the bottom surface 526. Each of the posts 528 and 529 has a hole 530 positioned at an end of each of the posts 528 and 529, respectively, away from the annular ring 522 and along a central axis of the posts 528 and 529, respectively. A pair of pullwires such as the pullwires 507 can be secured to the crown element 520, one at each of the posts 528 and 529. The edges of the annular ring 522 are curved or rounded, for example, with small radii, to eliminate breakage of the pullwires during multiple actuations.

Dimensions of the crown element 520 can vary in different embodiments depending on the dimensions of the flexible elongate member 108. In some embodiments, the annular ring 522 can have an outer radius 611 between about 5 FR and about 11 FR and an inner radius 612 between about 4 FR and about 10 FR. Each of the posts 528 and 529 can have a height 613 between about 1 mm and 3 mm and a width 614 between about 0.25 mm and 1.5 mm. Each hole 530 can have a radius 615 between about 0.05 mm and 0.7 mm. In some embodiments, the outer radius 611 can be less than the outer diameter of the flexible elongate member 108 while the inner radius 612 can be greater than the radius of the primary lumen of the flexible elongate member 108.

FIG. 7 is a side view of the crown element 520 taken along the line 601 of FIG. 6B with a pullwire 700 similar to the pullwires 507 in position according to embodiments of the present disclosure. The pullwire 700 can be composed of metal, hard plastic, or any suitable material. As shown, the pullwire 700 is anchored to the crown element 520 by forming a knot 710 at the post 528 creating segments 721 and 722 separated by the post 528. The post 528 provides connection security and stability when the segments 721 and 722 are actuated. The separation of the segments 721 and 722 by the post 528 allows actuations of the segments 721 and 722 to be independent of each other, and thus provides consistent bending of the ICE device 110 over multiple actuations of the segments 721 and 722. For example, an actuation of the segment 721 deflects the ICE device 110 in one direction and actuation of the segment 722 deflects the ICE device 110 in another direction. Another pullwire similar to the pullwires 700 and 507 can be anchored to the crown element 520 at the other post 529 using similar mechanisms to provide deflection of the ICE device 110 along a different plane. Thus, the crown element 520 enables independent and consistent actuations of the pullwire segments. In addition, the head 711 of the knot 710 is placed at the inner wall of the crown element 520 to minimize the amount of dissimilar material outside of the crown element 520 that can weaken the joint between the crown element 520 and the sleeve element 540 after bonding.

Figure 8B:
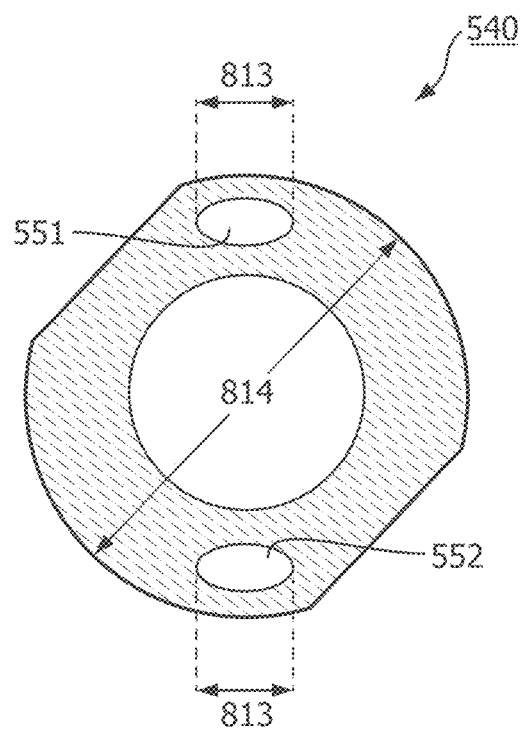
FIG. 8B is a top view of a sleeve element according to embodiments of the present disclosure.

FIG. 8A is a perspective view of the sleeve element 540 according to embodiments of the present disclosure. FIG. 8B is a top view of the sleeve element 540 according to embodiments of the present disclosure. The sleeve element 540 has a tubular body and includes flat outer surface portions 542 and 544 and curved outer surface portions 546 and 548. The sleeve element 540 is composed of a material compatible to the flexible elongate member 108 and the tip assembly 102. For example, the sleeve element 540 can be composed of a plastic polymer. The flat outer surface portions 542 and 544 have about the same surface area. The curved outer surface portions 546 and 548 have about the same surface area. The flat outer surface portion 542 is adjacent to the curved outer surface portions 546 and 548. The flat outer surface portion 544 is adjacent to the curved outer surface portions 546 and 548. The flat outer surface portions 542 and 544 are about radially opposite of each other. The sleeve element 540 further includes slots 551 and 552 extending longitudinally along the tubular body. The slot 551 is positioned proximal to the flat outer surface portion 542 and curved outer surface portion 546. The slot 552 is positioned proximal to the flat outer surface portion 544 and curved outer surface portion 548.

During assembly or manufacturing, the posts 528 and 529 of the crown element 520 are fitted into the slots 551 and 552, respectively, and thermally bonded. After the bonding, the holes 530 are filled with the material of the sleeve element 540. Thus, the holes 530 allow for a stronger bond and improve tensile strength at the joint between the crown element 520 and the sleeve element 540. Since the pullwires are anchored at the posts 528 and 529 and the posts 528 and 529 are fitted into the slots 551 and 552, respectively, the positioning of the slots 551 and 552 relative to the flat outer surface portions 542 and 544 can facilitate alignment of the pullwires to the imaging core 562 such that actuations of the pullwires can provide consistent articulation views, as described in greater detail herein.

Dimensions of the sleeve element 540 can vary in different embodiments depending on the dimensions of the flexible elongate member 108. For example, the outer diameter 814 may be smaller than the inner diameter of the proximal opening 568 of the tip member 560 such that the sleeve element 540 may be fitted into the proximal opening 568 of the tip member 560. The widths 813 of the slots 551 and 552 may be greater than the widths 614 of the posts 528 and 529 such that the posts 528 and 529 may be inserted into the slots 551 and 552, respectively. For example, the material of the sleeve element 540 may be pliable and may conform to the inserted posts 528 and 529.

Figure 9:
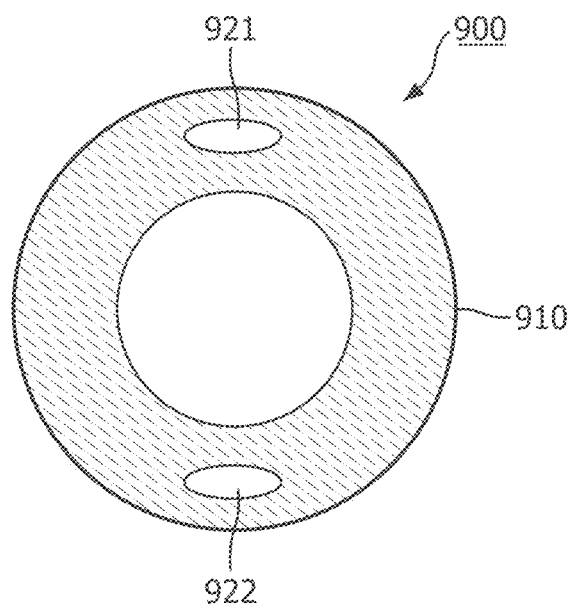
FIG. 9 is a top view of a sleeve element according to embodiments of the present disclosure.

FIG. 9 is a top view of a sleeve element 900 according to embodiments of the present disclosure. The sleeve element 900 can be employed by the ICE device 110 in place of the sleeve element 540. The sleeve element 900 is similar to the sleeve element 540, but has a curved outer surface 910 without any flat portion as in the sleeve element 540. The sleeve element 900 can include slots 921 and 922 similar to the slots 551 and 552, which can be used for fitting the posts 528 and 529, respectively, when bonded with the crown element. The sleeve element 900 can be used when the tip assembly 102 does not include an alignment portion for alignment. In some embodiments, a sleeve element can be shaped to have an outer surface portion different from remaining outer surface to allow for alignment, where the outer surface portion can be in any shape suitable for alignment.

Figure 10:
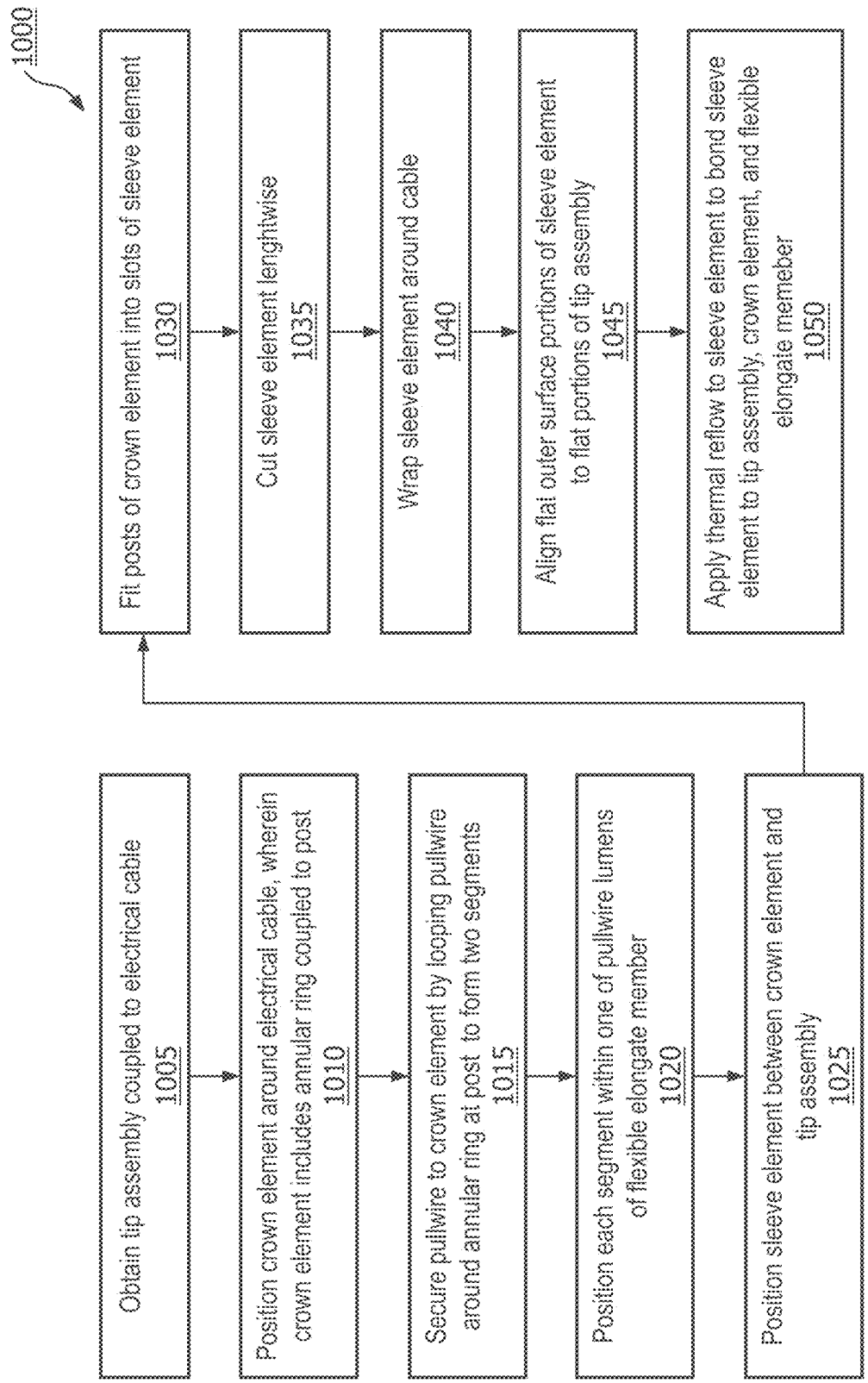
FIG. 10 is a flow diagram of a method of assembling an ICE device according to aspects of the disclosure.
Figure 11:
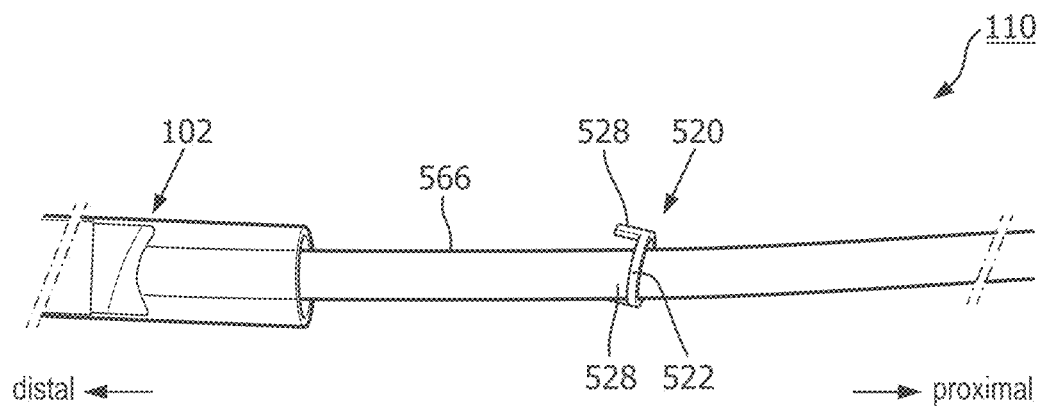
FIG. 11 is a schematic diagram illustrating a crown element fitted over an electrical cable, in a stage of assembly, according to embodiments of the disclosure.
Figure 12:
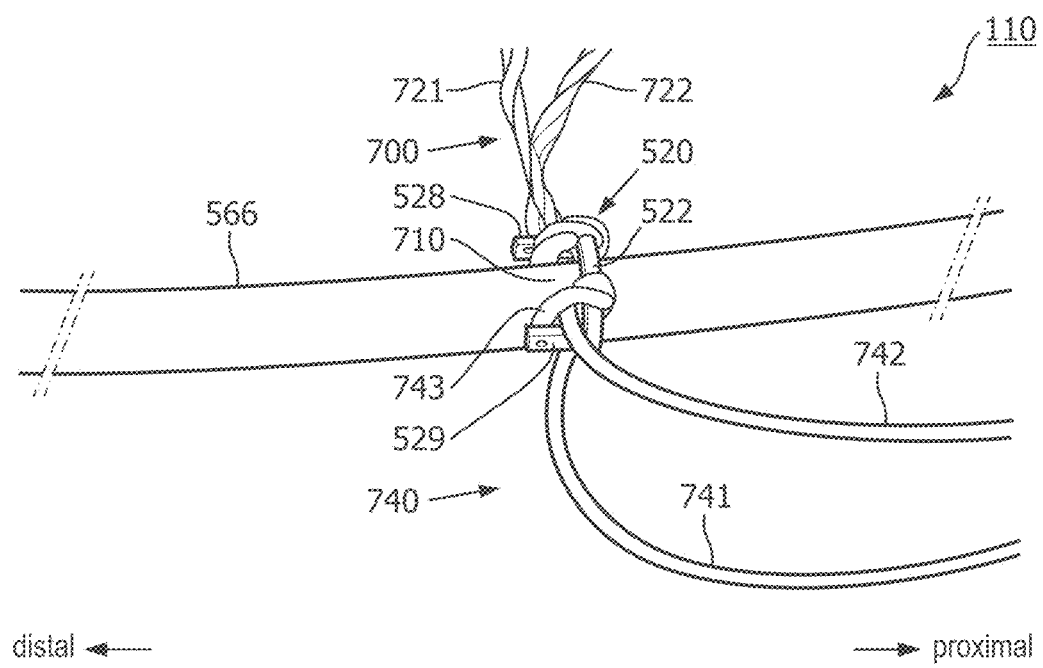
FIG. 12 is a schematic diagram illustrating a pair of pullwires anchored to a crown element, in a stage of assembly, according to embodiments of the disclosure.
Figure 13:
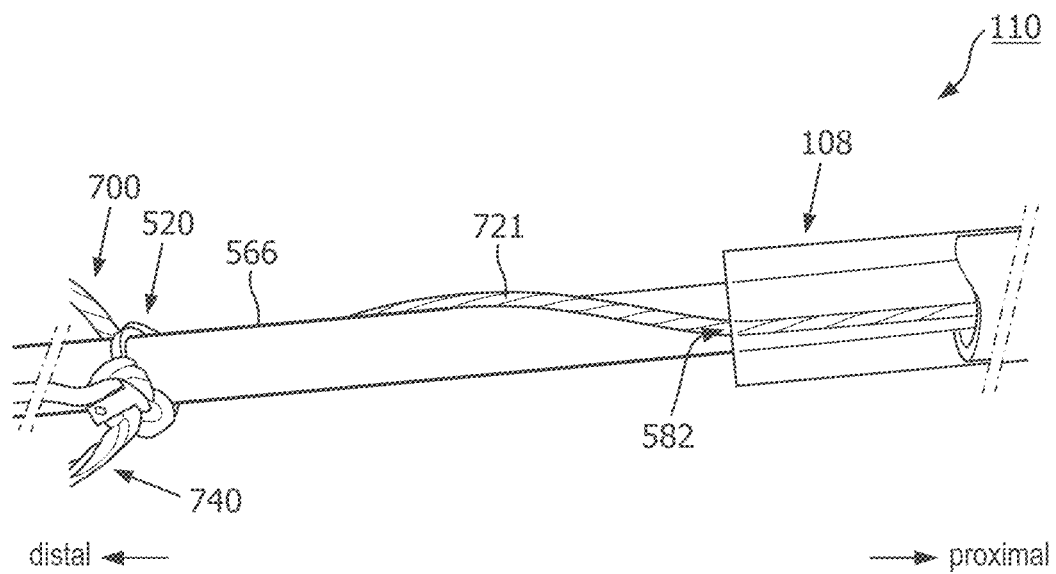
FIG. 13 is a schematic diagram illustrating a pair of pullwires anchored to a crown element and threaded through a flexible elongate member, in a stage of assembly, according to embodiments of the disclosure.
Figure 14:
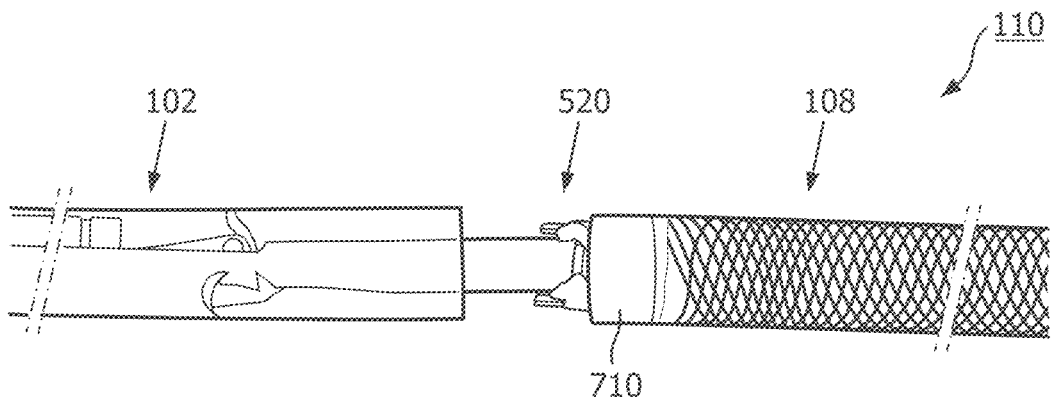
FIG. 14 is a schematic diagram illustrating a crown element positioned for coupling, in a stage of assembly, according to embodiments of the disclosure.
Figure 15:
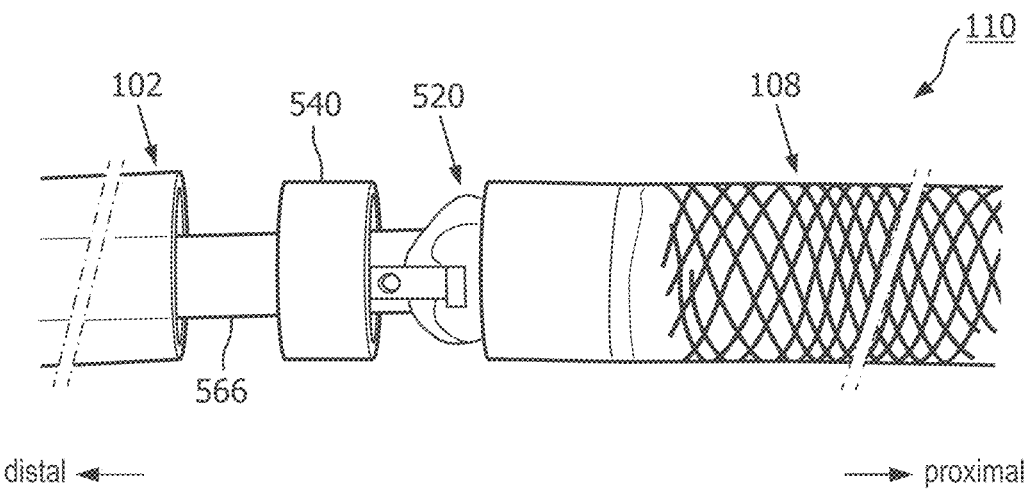
FIG. 15 is a schematic diagram illustrating a sleeve element positioned for coupling, in a stage of assembly, according to embodiments of the disclosure.
Figure 16:
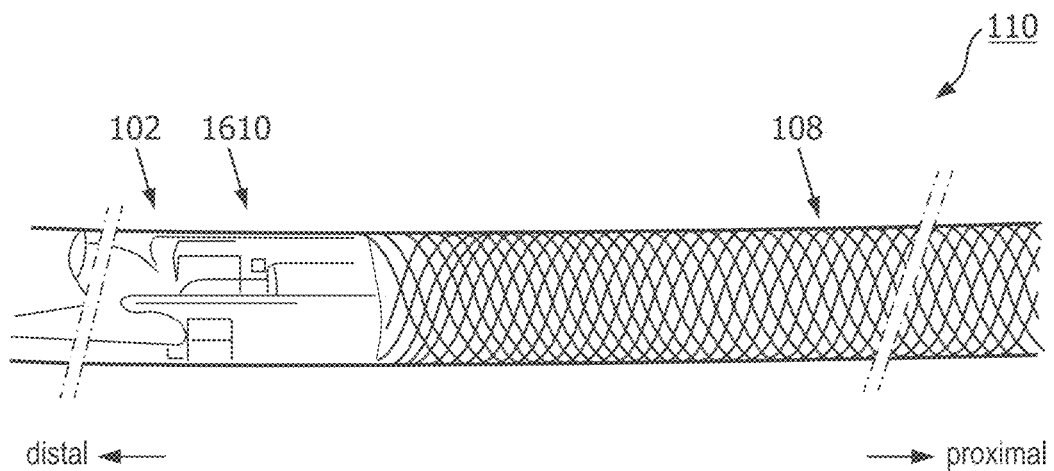
FIG. 16 is a schematic diagram illustrating a sleeve element bonded to a tip assembly and a flexible elongate member, in a stage of assembly, according to embodiments of the disclosure.

A method 1000 of assembling the ICE device 110 is described with reference made to FIGS. 10-16. FIG. 10 is a flow diagram of a method 1000 of assembling the ICE device 110 according to aspects of the disclosure. It is understood that additional steps can be provided before, during, and after the steps of method 1000, and some of the steps described can be replaced or eliminated for other embodiments of the method. The steps of the method 1000 can be carried out by a manufacturer of an ICE device. FIG. 11 is a schematic diagram illustrating the crown element 520 fitted over the electrical cable 566, in a stage of assembly, according to embodiments of the disclosure. FIG. 12 is a schematic diagram illustrating a pair of pullwires 700 and 740 anchored to the crown element 520, in a stage of assembly, according to embodiments of the disclosure. FIG. 13 is a schematic diagram illustrating the pair of pullwires 700 and 740 anchored to the crown element 520 and threaded through the flexible elongate member 108, in a stage of assembly, according to embodiments of the disclosure. FIG. 14 is a schematic diagram illustrating the crown element 520 positioned for coupling, in a stage of assembly, according to embodiments of the disclosure. FIG. 15 is a schematic diagram illustrating the sleeve element 540 positioned for coupling, in a stage of assembly, according to embodiments of the disclosure. FIG. 16 is a schematic diagram illustrating the sleeve element 540 bonded to the tip assembly 102 and the flexible elongate member 108, in a stage of assembly, according to embodiments of the disclosure.

Referring to the step 1005 of the method 1000, in an embodiment, the tip assembly 102 coupled to the electrical cable 566 is obtained. Referring to the step 1010 of the method 1000 and FIG. 11, in an embodiment, the crown element 520 is positioned around the electrical cable 566. FIG. 11 illustrates the electrical cable 566 pre-loaded with the crown element 520. As shown, the crown element 520 is positioned such that the posts 528 and 529 extend towards the tip assembly.

Referring to the step 1015 of the method 1000 and FIG. 12, in an embodiment, the pullwire 700 is secured to the crown element 520 by looping the pullwire 700 around the annular ring 522 at the post 528 to form the two segments 721 and 722. FIG. 12 illustrates a pair of pullwires 700 and 740 anchored to the crown element 520. The pullwire 700 is anchored to the annular ring 522 at the post 528 using similar knotting mechanisms shown in FIG. 7. Similarly, the pullwire 740 is anchored to the annular ring 522 at the post 529 by forming a Larks knot 743, which creates segments 741 and 742. It should be noted that the heads of the knots 710 and 743 are placed adjacent to the inner wall of the crown element 520. In an embodiment, the segments 721 and 722 are for steering the distal portion 104 and the tip assembly 102 in a left direction and an anterior direction, respectively. The segments 741 and 742 are for steering the distal portion 104 and the tip assembly 102 in a right direction and a posterior direction, respectively.

Referring to the step 1020 of the method 1000 and FIG. 13, in an embodiment, each segment 721 or 722 is positioned within one of a plurality of pullwire lumens 582 of the flexible elongate member 108. FIG. 13 illustrates the pair of pullwires 700 and 740 anchored to the crown element 520 and threaded through the flexible elongate member 108. As shown, the segment 721 is threaded through one of the pullwire lumens 582 of the flexible elongate member 108. Although not shown, each of the segments 722, 741, and 742 can be thread through one of the pullwire lumens 582.

Referring to the step 1025 of the method 1000 and FIGS. 14 and 15, in an embodiment, the sleeve element 540 is positioned between the crown element 520 and the tip assembly 102. FIG. 14 illustrates the crown element 520 positioned for coupling. As shown, the crown element 520 is positioned abutting the distal end of the flexible elongate member 108. FIG. 15 illustrates the sleeve element 540 positioned for coupling. As shown, the sleeve element 540 is positioned between the crown element 520 and the tip assembly 102.

Referring to the step 1030 of the method 1000, in an embodiment, the posts 528 and 529 are fitted into the slots 551 and 552, respectively, of the sleeve element 540.

Referring to the step 1035 of the method 1000, in an embodiment, the sleeve element 540 is cut lengthwise.

Referring to the step 1040 of the method 1000, in an embodiment, the sleeve element 540 is wrapped around the electrical cable 566.

Referring to the step 1045 of the method 1000, in an embodiment, the flat outer surface portions 542 and 544 are aligned to the flat portions of the tip assembly 102. The alignment is described in greater detail herein.

Referring to the step 1050 of the method 1000 and FIG. 16, in an embodiment, thermal reflow is applied to the sleeve element 540 to bond the sleeve element 540 to the tip assembly 102, the crown element 520, and the flexible elongate member 108. In FIG. 16, the bonding forms a joint 1610 between the tip assembly 102 and the flexible elongate member 108. As described above, the sleeve element 540 is composed of a material similar to the materials of the flexible elongate member 108 and the tip assembly 102 while the crown element 520 is composed of a dissimilar material that is thermoset. Thus, the thermal reflow can fuse the sleeve element 540 the flexible elongate member 108 and the tip assembly 102 together while the crown element 520 is embedded within the fused material. As such, the sleeve element 540 can fill the gap and/or space at the joint 1610. The sleeve element 540 can prevent collapse at the joint 1610 after the reflowing of different parts. In addition, the sleeve element 540 functions as a stopper in adding adhesive to the joint 1610 to maintain adhesive level at the surface of the joint. Further, the sleeve element 540 can increase the tensile strength of the joint 1610. In some embodiments, the crown element 520 and the sleeve element 540 are concentrically aligned to a primary lumen of the flexible elongate member 108.

The crown element 520 and the sleeve element 540 provide several benefits. The crown element 520 provides connection security and stability for individual pullwire segments 721, 722, 741, and 742 when the pullwire segments 721, 722, 741, or 742 is actuated in a proximal direction to deflect the tip assembly 102 and the distal portion 104 in a corresponding direction. In addition, the anchoring of the pullwires 700 and 740 at the posts 528 and 529, respectively, allow actuations of the pullwire segments 721, 722, 741, and 742 to provide consistent deflection angles. The holes 530 allow for bonding of the sleeve element 540 to the crown element 520 during the thermal reflow, and thus increasing the tensile strength. Further, the crown element 520 is shaped with rounded edges to prevent breakage of the pullwires 700 and 740 over actuations or increase the lifetime of the ICE device 110. The sleeve element 540 is shaped with the flat outer surface portions 542 and 544 to allow for easy, precise, and consistent alignment of the pullwires 700 and 740 to the imaging core 562. Thus, the employment of the sleeve element 540 allow for consistent angle of articulations. In addition, the sleeve element 540 can improve tensile strength at the joint between the tip assembly 102 and the flexible elongate member 108.

Figure 17:
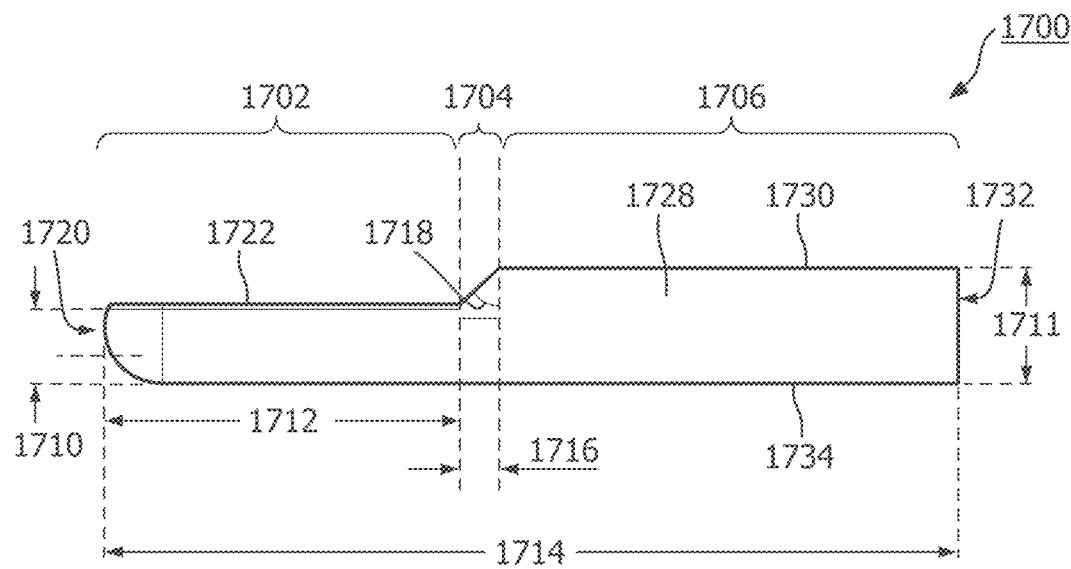
FIG. 17 is a side view of a tip member according to embodiments of the present disclosure.

FIG. 17 is a side view of a tip member 1700 according to embodiments of the present disclosure. The tip member 1700 can be employed by the tip assembly 102 in place of the tip member 560. The tip member 1700 has a tubular body 1728 with a closed round distal tip 1720 and an opened proximal end 1732. The tip member 1700 includes a distal portion 1702, a tapered portion 1704, and a proximal portion 1706 coupled in order from the closed round distal tip 1720 to the opened proximal end 1732. The tip member 1700 includes a curved bottom outer wall 1734 coupled to a proximal curved top outer wall 1730 at the proximal portion 1706 that smoothly transitions into a distal flat top outer wall 1722 at the distal portion 1702. The smooth radius transition at the tapered portion 1704 eliminates the need of a perpendicular surface to join the distal flat top outer wall 1722 and the proximal curved top outer wall 1730. As such, the outer geometry of the tip member 1700 reduces friction and provides smooth surfaces to avoid catching on tissue structures when the tip member 1700 traverses through a patient body and reduces trauma to the patient. In some embodiments, the tip member 1700 can additionally be treated with a hydrophilic material to further reduce friction.

The tubular body 1728 can be composed of a thermoplastic elastomer material or any suitable biocompatible material that has acoustic impedance matching to blood within a vessel of a patient body when in use. In an embodiment, the tip member 1700 is constructed from a Pebax® polyether block amides 3533 SA 01 MED material. Dimensions of the tip member 1700 can vary in different embodiments. In an embodiment, the tip member 1700 is constructed from a Pebax® polyether block amides 3533 SA 01 MED material. Dimensions of the tip member 1700 can vary in different embodiments. In some embodiments, the tip member 1700 can include a length 1714 between about 15 mm to about 30 mm. The distal flat top outer wall 1722 can extend a length 1712 between about 5 mm to about 15 mm. The tip member 1700 can include a height 1710 proportional to the outer diameter 1711 of the tip member 1700. In some embodiment, the height 1710 is at least about 50% of the outer diameter 1711, with some particular embodiments between about 50% to about 75% of the outer diameter 1711. The tapered portion 1704 can extend a length 1716 between about 0.5 mm to about 2 mm and tapers at an angle 1718 between about 15 degrees to about 75 degrees relative to a central longitudinal axis of the tip member 1700.

Figure 18:
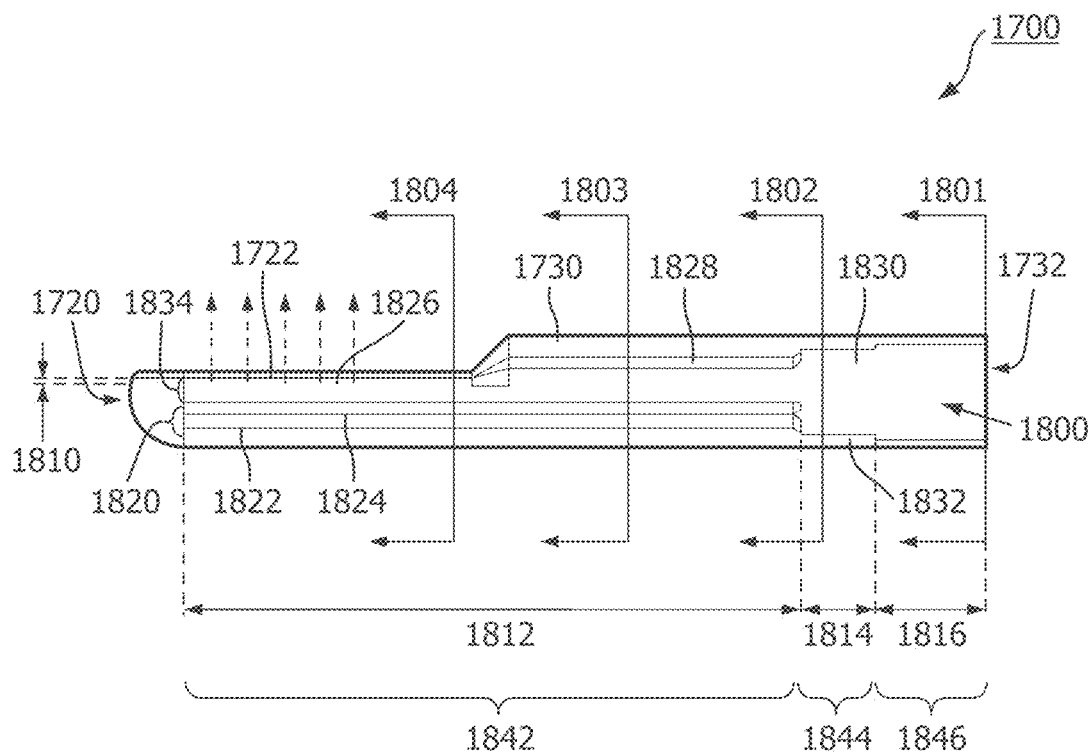
FIG. 18 is a side perspective view of a tip member according to embodiments of the present disclosure.

FIG. 18 is a side perspective view of the tip member 1700 according to embodiments of the present disclosure. The tip member 1700 includes an inner cavity 1800 having an interface portion 1846, an alignment portion 1844, and a receiving portion 1842 coupled in order from the opened proximal end 1732 towards the closed round distal tip 1720. In addition, the inner cavity 1800 includes a chamber 1834 adjacent and distal to the receiving portion 1842 used for accommodating kerf seal as described in greater detail herein.

The interface portion 1846 is sized and shaped to couple to the flexible elongate member 108, for example, via the sleeve element 540. The alignment portion 1844 is sized and shaped to align to the sleeve element 540 or any suitable connecting member. In an embodiment, the alignment portion 1844 is molded to form alignment members 1830 and 1832 along an inner wall portion of the inner cavity 1800. In an embodiment, the alignment members 1830 and 1832 are configured to have first keyed surfaces inter-engaging with second keyed surfaces (e.g., flat outer surface portions 542 and 544) of the sleeve element 540.

The receiving portion 1842 is sized and shaped to receive the imaging core 562. The geometry of the receiving portion 1842 is configured to facilitate the alignment and positioning of the imaging core 562. The receiving portion 1842 includes a proximal curved top inner wall 1828 that smoothly transitions into a distal flat top inner wall 1826. The proximal curved top inner wall 1828 is opposite the proximal curved top outer wall 1730 and the distal flat top inner wall 1826 is opposite the distal flat top outer wall 1722. In an embodiment, the receiving portion 1842 is molded to form a guide member 1820 having a stepped ledge with a first step 1822 and a second step 1824 extending longitudinally along a sidewall portion of the receiving portion 1842. The receiving portion 1842 can include another guide member 1850 (shown in FIG. 19) similar to the guide member 1820 extending longitudinally along a radially opposite sidewall portion of the receiving portion 1842. The distal flat top inner wall 1826 and the guide members 1820 and 1850 restrict the positioning of the imaging core 562 within the receiving portion 1842. In an embodiment, the imaging core 562 includes an array of ultrasound transducer elements and is positioned such that ultrasonic waves propagates towards and through the distal flat top inner wall 1826 and the distal flat top outer wall 1722 as shown by the dashed arrows and described in greater details herein. The alignment members 1830 and 1832 are positioned in a pre-defined relation to an orientation of the imaging core 562.

Dimensions of the tip member 1700 can vary in different embodiments. In some embodiments, the tip member 1700 includes a uniform thickness 1810 between the distal flat top inner wall 1826 and the distal flat top outer wall 1722 of less than 200 microns such that distortion such as reflection and attenuation of the ultrasonic waves may be minimized. The receiving portion 1842 can extend a length 1812 between about 10 mm to about 28 mm. The alignment portion 1844 can extend a length 1814 between about 1 mm to about 5 mm. The interface portion 1846 can extend a length 1816 between about 1 mm to about 5 mm.

Figure 19:
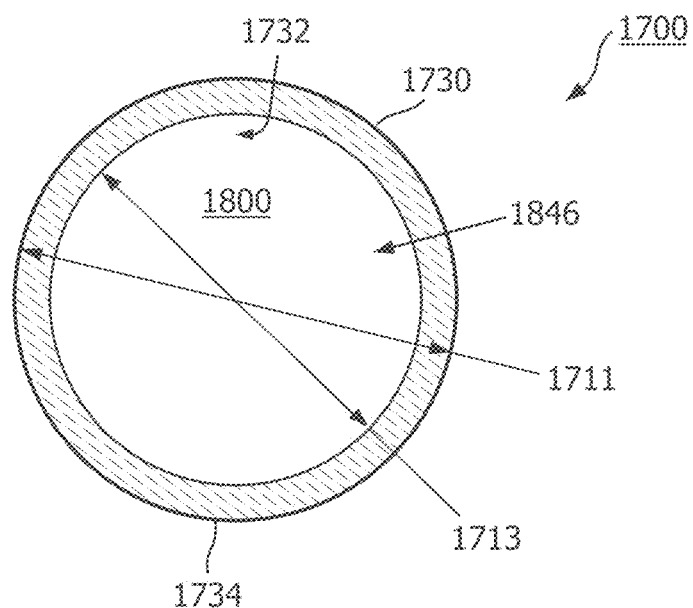
FIG. 19 is a cross-sectional view of a tip member according to embodiments of the present disclosure.

FIG. 19 is a cross-sectional view of the tip member 1700 taken along the line 1801 of FIG. 18 according to embodiments of the present disclosure. FIG. 19 illustrates the opened proximal end 1732 with interface portion 1846 of the inner cavity 1800. Dimensions of the opened proximal end 1732 can vary in different embodiments. In some embodiments, the proximal opened end 1732 has a substantially circular shape. The outer diameter 1711 and the inner diameter 1713 may be sized to match the body of a catheter shaft (e.g., the flexible elongate member 108) such that the tip member 1700 can be coupled to the catheter shaft. For example, a catheter shaft body between about 8 FR and about 12 FR may have a wall thickness between about 100 microns and about 400 microns. To couple to such a catheter shaft, the outer diameter 1711 may be between about 8 FR and about 12 FR and a difference between outer diameter 1711 and the inner diameter 1713 may be between about 100 microns and about 400 microns.

Figure 20:
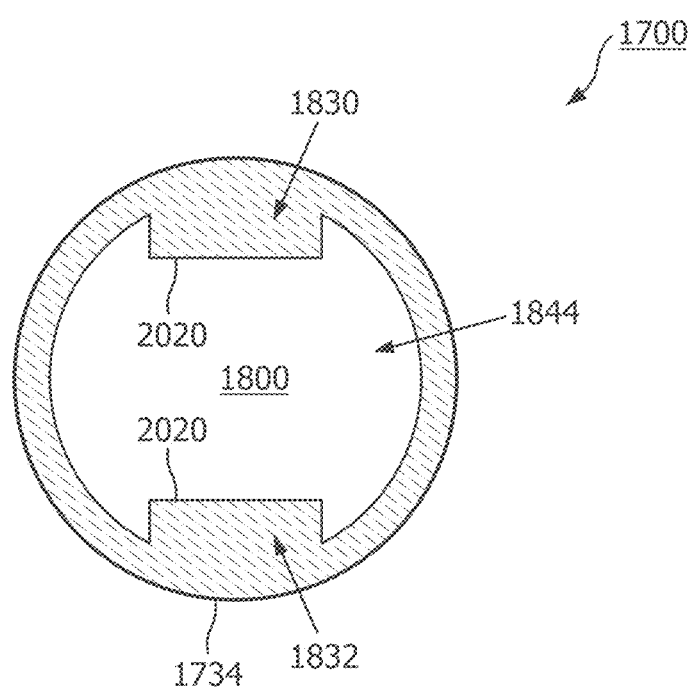
FIG. 20 is a cross-sectional view of a tip member according to embodiments of the present disclosure.

FIG. 20 is a cross-sectional view of the tip member 1700 taken along the line 1802 of FIG. 18 according to embodiments of the present disclosure. FIG. 20 illustrates the alignment portion 1844 of the inner cavity 1800. The tip member 1700 is molded to form the alignment members 1830 and 1832 along portions of the inner wall of the alignment portion 1844. For example, the alignment members 1830 and 1832 are ledges extending transversely across the portions of the inner wall and positioned radially opposite of each other. Each ledge has a flat surface 2020 about perpendicular to the ultrasonic beam propagate direction of the imaging core 562. Dimensions of the alignment members 1830 and 1832 can vary in different embodiments. For example, the alignment members 1830 and 1832 may be shaped and sized to adapt to the sleeve element 540 (e.g., the flat outer surface portions 542 and 544) such that the sleeve element 540 and the tip member 1700 may be aligned by inter-engaging the alignment members 1830 and 1832 with the flat outer surface portions 542 and 544.

Figure 21:
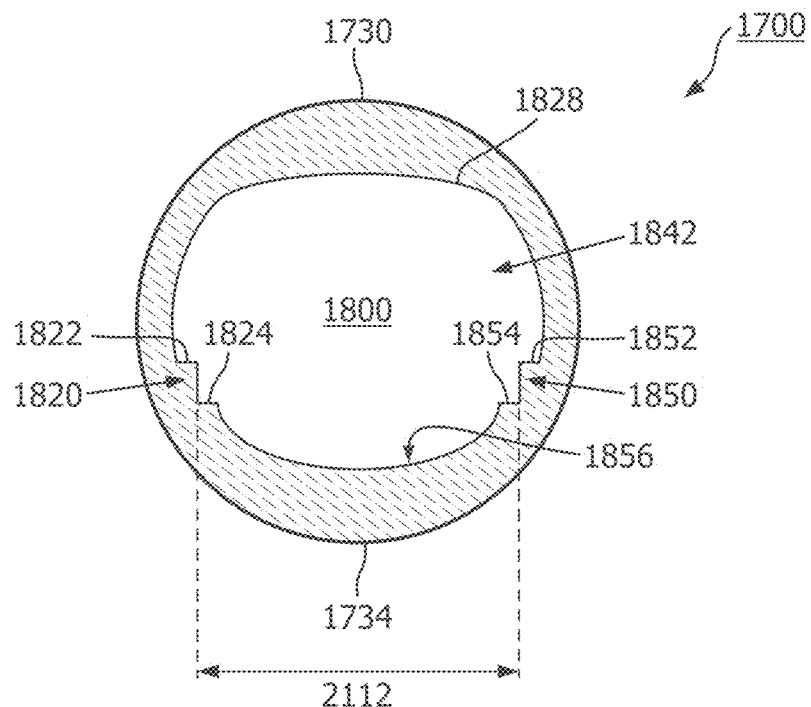
FIG. 21 is a cross-sectional view of a tip member according to embodiments of the present disclosure.

FIG. 21 is a cross-sectional view of the tip member 1700 taken along the line 1803 according to embodiments of the present disclosure. FIG. 21 illustrates the receiving portion 1842 of the inner cavity 1800, where the tip member 1700 has the proximal curved top outer wall 1730 and the proximal curved top inner wall 1828. The tip member 1700 is molded to form the guide members 1820 and 1850 along portions of the inner wall of the receiving portion 1842. The guide members 1820 and 1850 are positioned radially opposite of each other within the receiving portion 1842. The guide member 1820 includes the step ledge with the first step 1822 and the second step 1824. Similarly, the guide member 1850 includes a step ledge with a first step 1852 and a second step 1854. In addition, the tip member 1700 is molded to form a raised U-shaped bottom inner wall 1856 extending longitudinally along the receiving portion 1842 and coupled to the guide members 1820 and 1850. As described in greater detail herein, the guide members 1820 and 1850 restrict the positioning of the imaging core 562 (not shown). Dimensions of the guide members 1820 and 1850 and the raised U-shaped bottom inner wall 1856 can vary in different embodiments. For example, the dimensions of the guide members 1820 and 1850 and the separation distance 2112 between the guide members 1820 and 1850 are shaped and sized to accommodate the imaging core 562. The wall thickness of the raised U-shaped bottom inner wall 1856 is configured to minimize acoustic attenuation.

Figure 22:
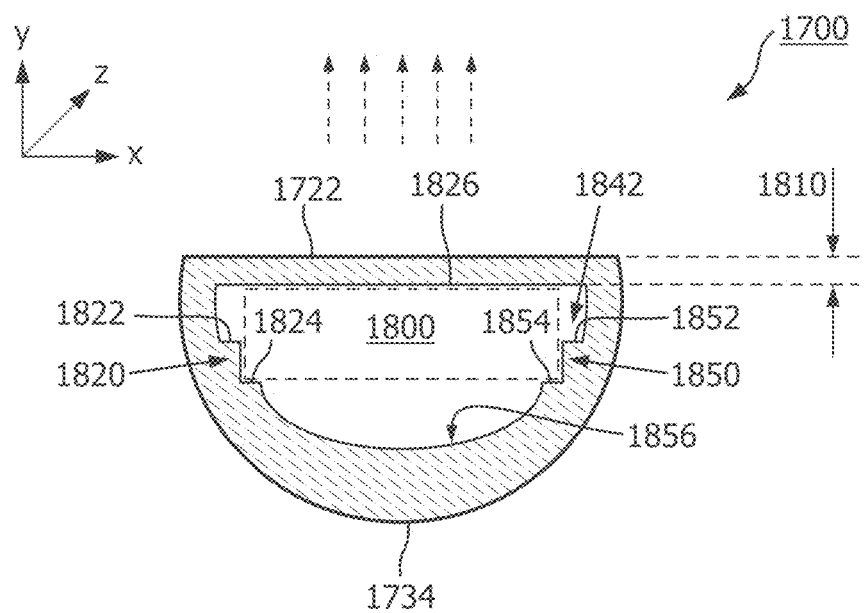
FIG. 22 is a cross-sectional view of a tip member according to embodiments of the present disclosure.

FIG. 22 is a cross-sectional view of the tip member 1700 taken along the line 1804 according to embodiments of the present disclosure. FIG. 22 illustrates the receiving portion 1842 of the inner cavity 1800, where the tip member 1700 has the distal flat top outer wall 1722 and the distal flat top inner wall 1826. The guide members 1820 and 1850 and the distal flat top inner wall 1826 restrict the positioning of the imaging core 562. For example, the imaging core 562 can be positioned in the tip member 1700 guided by the guide members 1820 and 1850 and the distal flat top inner wall 1826 as shown by the dashed box. The guide members 1820 and 1850 restrict the positioning of the imaging core 562 along a first axis and in a first direction along a second axis about perpendicular to the first axis. In FIG. 22, the first axis is shown as the x-axis and the second axis is shown as the y-axis. The distal flat top inner wall 1826 restricts the positioning of the imaging core 562 in an opposite direction along the second axis. As described above, the tip member 1700 is sized such that the thickness 1810 between the distal flat top outer wall 1722 and the distal flat top inner wall 1826 is less than 200 micron to minimize distortions such as reflections and/or deflections of ultrasonic waves (dashed arrows) produced by the imaging core 562 during operation.

Figure 23:
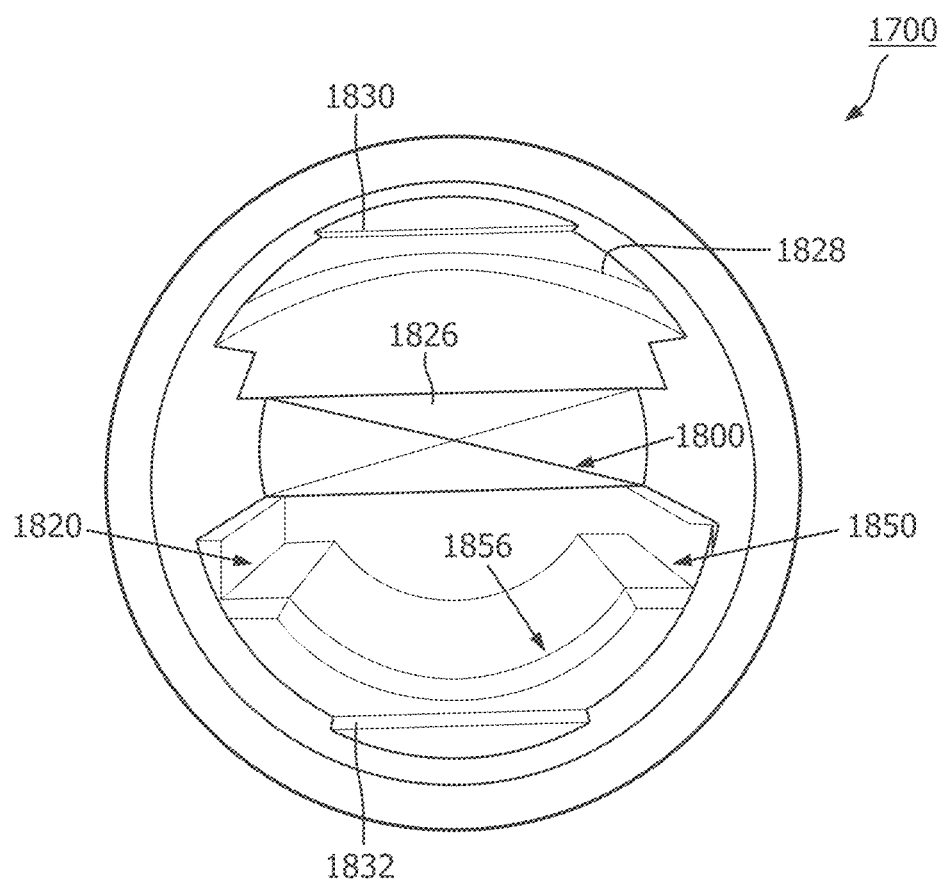
FIG. 23 is a back perspective view of a tip member according to embodiments of the present disclosure.

FIG. 23 is a back perspective view of the tip member 1700 according to embodiments of the present disclosure. FIG. 23 illustrates the structure of the inner cavity 1800 viewing from the opened proximal end 1732 as shown by the line 1801. As shown, the inner cavity 1800 includes the alignment member 1830 and 1832, the raised U-shaped bottom inner wall 1856, the guide members 1820 and 1850, and the distal flat top inner wall 1826. The raised U-shaped bottom inner wall 1856 is adjacent and distal to the alignment member 1832 and coupled to the guide members 1820 and 1850.

Figure 24:
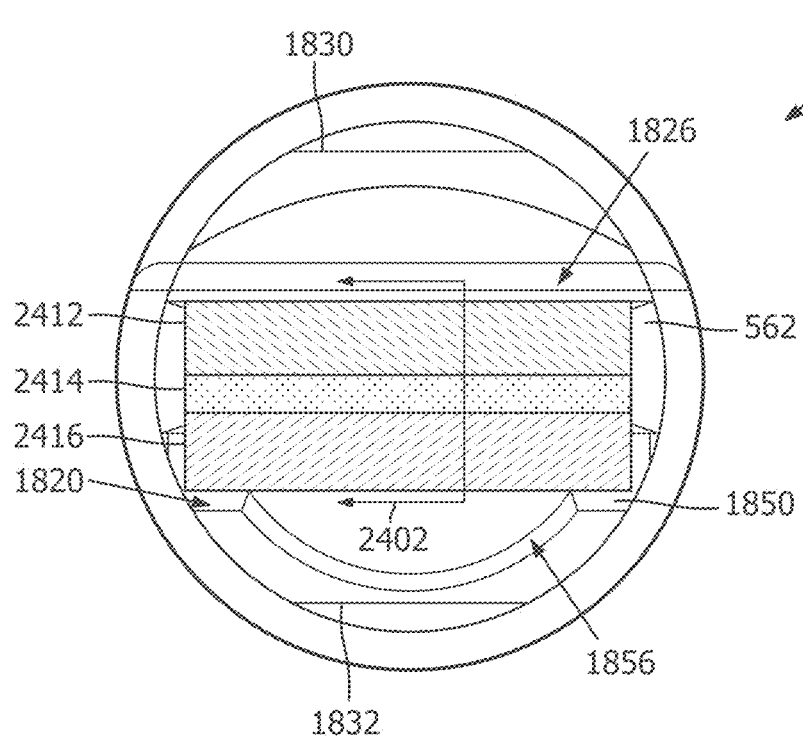
FIG. 24 is a back perspective view of a tip member with an imaging core in position according to embodiments of the present disclosure.

FIG. 24 is a back perspective view of the tip member 1700 with the imaging core 562 in position according to embodiments of the present disclosure. FIG. 24 illustrates the positioning of the imaging core 562 in the inner cavity 1800 viewing from the opened proximal end 1732 as shown by the line 1801. The imaging core 562 is encased within the inner cavity 1800 guided by the guide members 1820 and 1850 and the distal flat top inner wall 1826. The imaging core 562 can include a transducer circuit layer 2414 embedded between an acoustic stack 2412 and a backing material layer 2416. The transducer circuit layer 2414 includes ultrasound transducer elements and associated circuitry. The acoustic stack 2412 is composed of materials acoustically matched to the ultrasound transducer elements, the transmission medium, and the target tissue for imaging. The backing material layer 2416 is composed of an acoustically absorptive material so that the backing material layer 2416 can absorb or deaden the ultrasonic waves coming from the back of the transducer circuit layer 2414. For example, the acoustic stack 2412 can include materials such as PZT, single crystal, CMUT, PMUT, etc. and the backing material layer 2416 can include an epoxy material. The acoustic stack 2412 is positioned almost against the distal flat top inner wall 1826, creating a thin bond line to further minimize acoustic distortion of the ultrasonic waves. The spaces of the inner cavity 1800 are filled with an encapsulating material to enclose the imaging core 562. For example, the encapsulating material may include polydimethylsiloxane (PDMS), polyurethane, ultraviolet (UV) adhesives, or any suitable material that have desirable characteristics such as acoustic properties, bonding strength, and ease to work with during manufacturing. In some embodiments, the acoustic stack 2412 includes non-filled air kerfs, for example, along a perimeter of the acoustic stack 2412. In such embodiments, the perimeter of the acoustic stack 2412 is sealed with a sealing material such as an UV adhesive to seal the non-filled air kerfs prior to filling the inner cavity 1800 with the encapsulating material. The chamber 1834 shown in FIG. 18 can be used to accommodate the sealing material.

Figure 25:
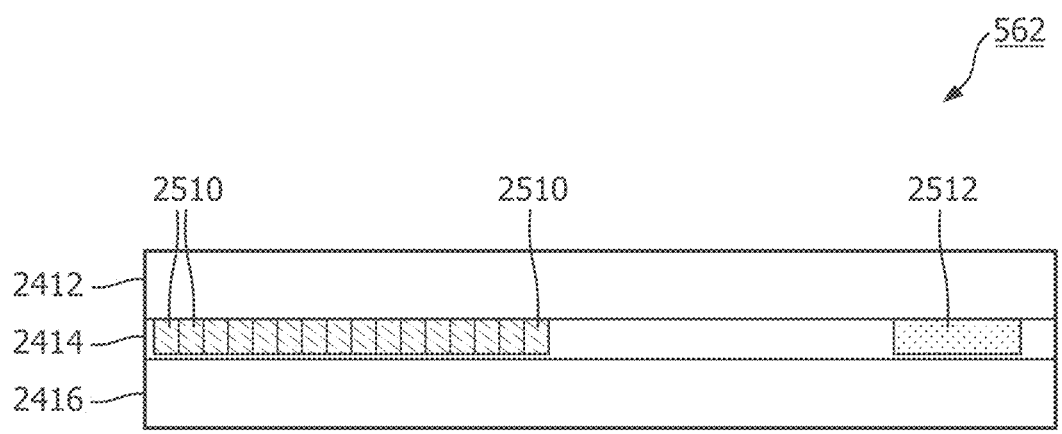
FIG. 25 is a cross-sectional side view of an imaging core according to embodiments of the present disclosure.

FIG. 25 is a cross-sectional side view of the imaging core 562 taken along the line 2402 of FIG. 24 according to embodiments of the present disclosure. The transducer circuit layer 2414 includes an array of ultrasound transducer elements 2510 coupled to one or more multiplexer chips 2512, for example, via conductive traces and/or associated circuitry. In some embodiments, the number of ultrasound transducer elements 2510 may be 8, 16, 32, 64, or any suitable number. The ultrasound transducer elements 2510 are composed of piezoelectric material. Exemplary transducers for ICE have a typical thickness of approximately 0.28 mm in the piezoelectric material to enable an 8 megahertz (MHz) ultrasound signal to be generated and transmitted at a typical velocity of 1500 meter per second (m/sec) through blood. The transducer thickness can be of various thicknesses ranging approximately from 0.56 mm to 0.19 mm to generate sufficient penetration depth in tissue imaging. In general, the thickness of the transducers can be adjusted for the frequency of sound in the transmission medium for the desired penetration depth in any tissue imaging. Image intensity can be adjusted by driving voltage on the transducers.

The multiplexer chips 2512 multiplex control signals, for example, generated by the processing system 130, and transfer the control signals to corresponding ultrasound transducer elements 2510. The controls signals can control the emission of ultrasound pulses and/or the reception of echo signals. In the reverse direction, the multiplexer chips 2512 multiplexes echo signals reflected by target tissue and received by the ultrasound transducer elements 2510 multiplexer chips 2512 and transfer the received echo signals, for example, to the processing system 130 for processing and/or display.

FIG. 26 is a perspective view of the tip assembly 102 and the sleeve element 540 positioned for coupling according to embodiments of the present disclosure. The tip assembly 102 is illustrated with the imaging core 562 in position within the tip member 1700. The imaging core 562 is coupled to the electrical cable 566 via the electrical interconnection 564. The electrical cable 566 extends through the alignment portion 1844 and the interface portion 1846 of the inner cavity 1800 and sleeve element 540. The electrical cable 566 can further extend through the flexible elongate member 108 as shown in FIG. 5. During manufacturing, the interface portion 1846 can extend over and cover a portion of the sleeve element 540, the crown element 520, and the flexible elongate member 108, thus improving the bonding strength.

As shown, the tip member 1700 is oriented such that the alignment members 1830 and 1832 are aligned to the flat outer surface portions 542 and 544 of the sleeve element 540. As described above, the sleeve element 540 includes the flat outer surface portions 542 and 544 and the slots 551 and 552, which are configured to couple to the crown element 520 in a particular orientation associated with the positioning of the pullwires 700 and 740. Thus, the sleeve element 540, the alignment members 1830 and 1832, and the crown element 520 can be conjunctively designed to allow coupling of the sleeve element 540, the alignment members 1830 and 1832, and the crown element 520 in a particular orientation. As such, the sleeve element 540, the alignment members 1830 and 1832, and the crown element 520 can be consistently aligned during manufacturing without additional alignment measurement or adjustment. Since the alignment members 1830 and 1832 are oriented in a predefined relation with the ultrasound beam propagation direction of the imaging core 562 and the pullwires 700 and 740 are configured to provide steering of the tip assembly 102, the actuations of the pullwires 700 and 740 can provide consistent articulation view for imaging. It should be noted that the alignment keying of the sleeve element 540 and the alignment members 1830 and 1832 can be alternatively configured as determined by a person of ordinary skill in the art to achieve similar functionalities.

The configuration and structure of the tip member 1700 described above provide several benefits such as safe and easy delivery for catheterization, improved tensile strength for steering or navigation, consistent or automatic alignment, and improved image quality. For example, the outer geometry of the tip member 1700 is configured to provide smooth surfaces and smooth edges with small radii. The smooth edges reduce friction when the tip member 1700 traverses a vessel during insertion. The smooth surfaces prevent tears and/or damages to tissue structures during the insertion. The smooth, radius transition from the proximal curved top outer wall 1730 to the distal flat top outer wall 1722 ensure that there are no ledges that can catch on outer features during the insertion. In addition, the smooth edges and smooth surfaces can facilitate crossing of a septum or other anatomical feature during a catheterization procedure. The material type and the wall thickness (e.g., the uniform thickness 1810) of the tip member 1700 are selected to minimize acoustic distortion, attenuation, and/or reflection. The internal geometry of the tip member 1700 is configured to facilitate alignment during manufacturing. As described, the alignment members 1830 and 1832 provide consistent and predictable alignment between the imaging core 562 and the pullwires 700 and 740. The tip member 1700 can also include other features, for example, a guidewire lumen, holes, or other geometry to accommodate additional devices or features such as pressure sensors, drug delivery mechanisms, and/or any suitable interventional features.

Figure 27:
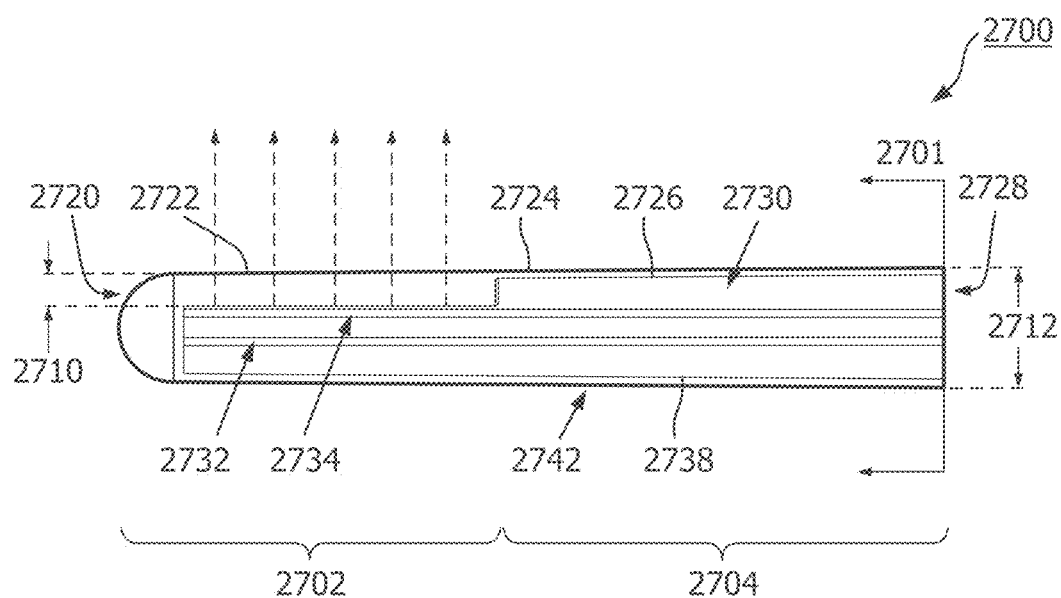
FIG. 27 is a side perspective view of a tip member according to embodiments of the present disclosure.

FIGS. 27-30 illustrate alternative tip member configurations that can provide substantially similar benefits as the tip member 1700. FIG. 27 is a side perspective view of a tip member 2700 according to embodiments of the present disclosure. The tip member 2700 can be employed by the tip assembly 102. The tip member 2700 has a tubular body 2742 with a closed round distal end 2720 and an opened proximal end 2728. The tip member 2700 includes a distal portion 2702 and a proximal portion 2704. The tip member 2700 includes a curved outer wall 2724. For example, the tip member 2700 has a uniform external circular profile. In some embodiments, the curved outer wall 2724 can be designed to provide a lens effect to focus ultrasonic waves. The tubular body 2742 can be constructed from similar materials as the tubular body 1728 of the tip member 1700 member.

The tip member 2700 includes an inner cavity 2730 extending from the closed proximal end 2728 towards the closed round distal end 2720. The inner cavity 2730 is configured to receive the imaging core 562. The inner cavity 2730 includes a proximal curved top inner wall 2726 at the proximal portion 2704 and a distal flat top inner wall 2722 at the distal portion 2702. The inner cavity 2730 includes a curved bottom inner wall 2738 coupled to the proximal curved top inner wall 2726 and the distal flat top inner wall 2722. The inner cavity 2730 is molded to form a pair of rails 2732 and 2734 extending along a sidewall portion of the inner cavity 2730 from the proximal opened end 2728 towards the closed round distal end 2720. The rails 2732 and 2734 are circumferentially spaced apart from each other forming a space for positioning the imaging core 562. The inner cavity 2730 further includes another pair of rails 2752 and 2754 (shown in FIG. 28) similar to the rails 2732 and 2734 extending longitudinally along a radially opposite sidewall portion of the inner cavity 2730. Thus, the rails 2732, 2734, 2752, and 2754 operate as guide members to restrict the positioning of the imaging core 562. For example, the imaging core 562 is positioned such that the ultrasound transducer elements 2510 emit ultrasonic waves towards and through the distal flat top inner wall 2722 and curved outer wall 2724 at the distal portion 2702 as shown by the dashed arrows. Dimensions of the tip member 2700 can be substantially similar to the tip member 1700, but the wall thickness 2710 at the distal portion 2702 is greater than 200 microns. For example, the wall thickness 2710 can be between about 25% and about 50% of the outer diameter 2712 of the tip member 2700.

Figure 28:
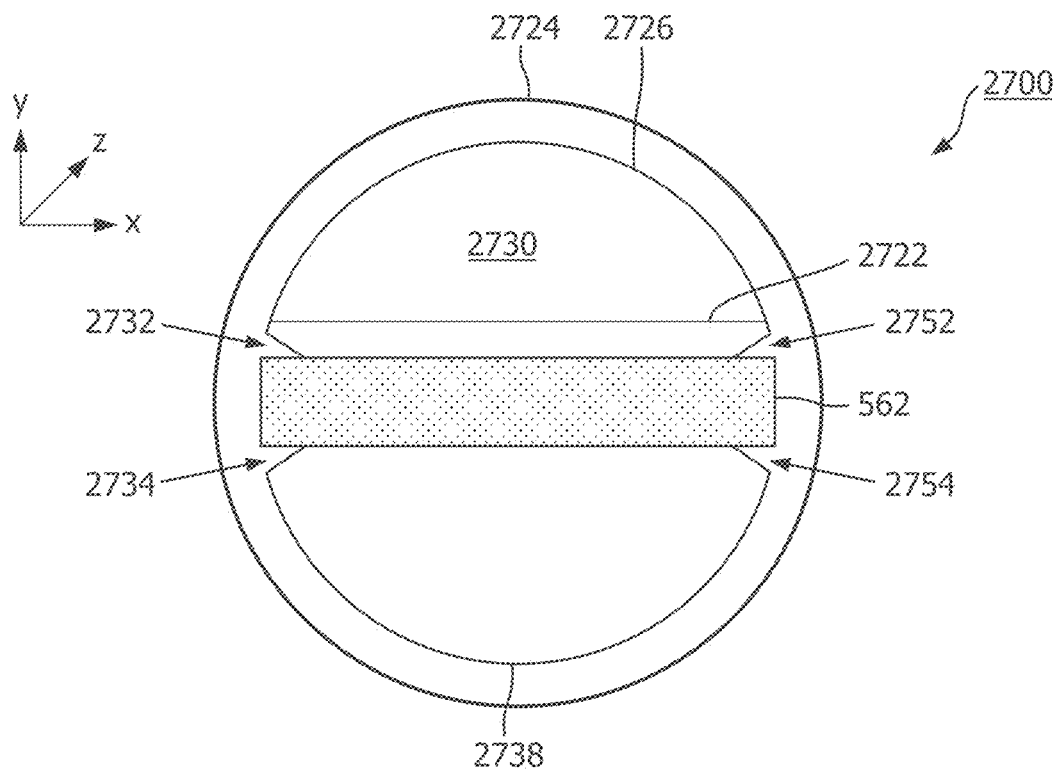
FIG. 28 is a back perspective view of a tip member with an imaging core in position according to embodiments of the present disclosure.

FIG. 28 is a back perspective view of the tip member 2700 with the imaging core 562 in position according to embodiments of the present disclosure. FIG. 28 illustrates the positioning of the imaging core 562 in the inner cavity 2730 viewing from the opened proximal end 2728 as shown by the line 2701. The imaging core 562 is encased within the inner cavity 2730 guided by the rails 2732, 2734, 2752, and 2754 along a first axis and a second axis about perpendicular to the first axis. In FIG. 28, the first axis is shown as the x-axis and the second axis is shown as the y-axis. The positioning of the imaging core 562 along the z-axis is restricted by the farthest distal end of the inner cavity 2730. The spaces between the inner cavity 2730 and the imaging core 562 are filled with similar encapsulating material as used for the inner cavity 1800 of the tip member 1700. The tip member 2700 can further include alignment members similar to the alignment members 1830 and 1832 to facilitate alignment with the sleeve element 540, the crown element 520, and the flexible elongate member 108.

Figure 29:
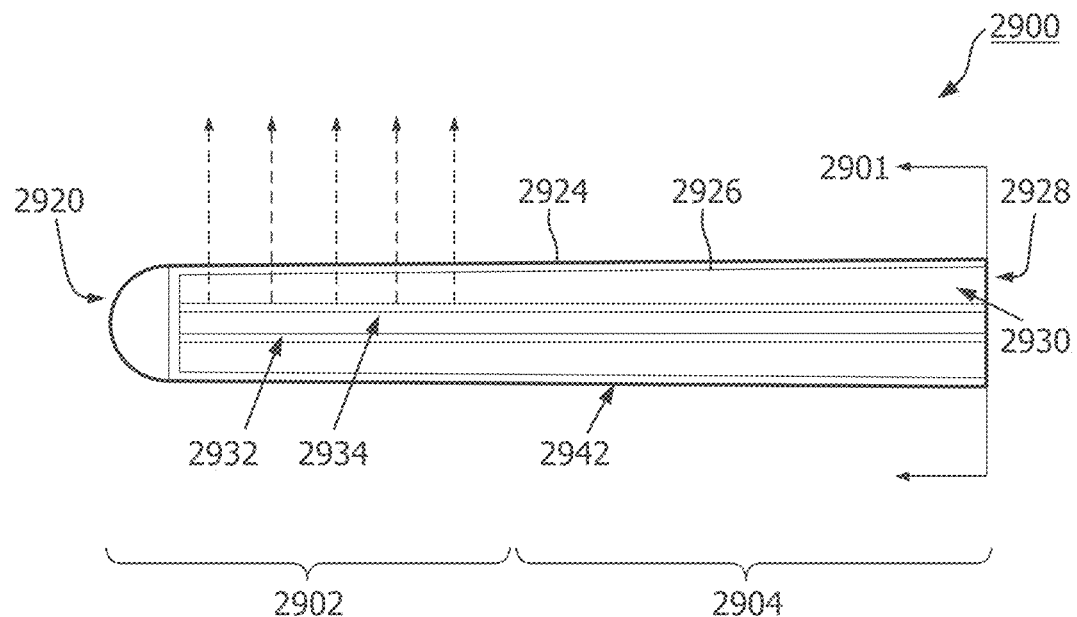
FIG. 29 is a side perspective view of a tip member according to embodiments of the present disclosure.

FIG. 29 is a side perspective view of a tip member 2900 according to embodiments of the present disclosure. The tip member 2900 can be employed by the tip assembly 102. The tip member 2900 is similar to the tip member 2700, but has a different internal geometry. The tip member 2900 has a tubular body 2942 with a closed round distal end 2920 and an opened proximal end 2928. The tip member 2900 includes a distal portion 2902 and a proximal portion 2904. The tip member 2900 includes a curved outer wall 2924. The tubular body 2942 can be constructed from similar materials as the tubular body 1728 of the tip member 1700 member and the tubular body 2742 of the tip member 2700 member.

The tip member 2900 includes an inner cavity 2930 extending from the closed proximal end 2928 towards the closed round distal end 2920. The inner cavity 2930 is configured to receive the imaging core 562. The inner cavity 2930 includes a curved inner wall 2926. The inner cavity 2930 is molded to form a pair of rails 2932 and 2934 extending along a sidewall portion of the inner cavity 2930 from the proximal opened end 2928 towards the closed round distal end 2920. The rails 2932 and 2934 are circumferentially spaced apart from each other forming a space for positioning the imaging core 562. The inner cavity 2930 further includes another pair of rails 2952 and 2954 (shown in FIG. 30) similar to the rails 2932 and 2934 extending longitudinally along a radially opposite sidewall portion of the inner cavity 2930. Thus, the rails 2932, 2934, 2952, and 2954 operate as guide members to restrict the positioning of the imaging core 562. For example, the imaging core 562 is positioned such that the ultrasound transducer elements 2510 emit ultrasonic waves towards and through a portion of the curved inner wall 2926 and a portion of curved outer wall 2924 at the distal portion 2902 as shown by the dashed arrows.

Figure 30:
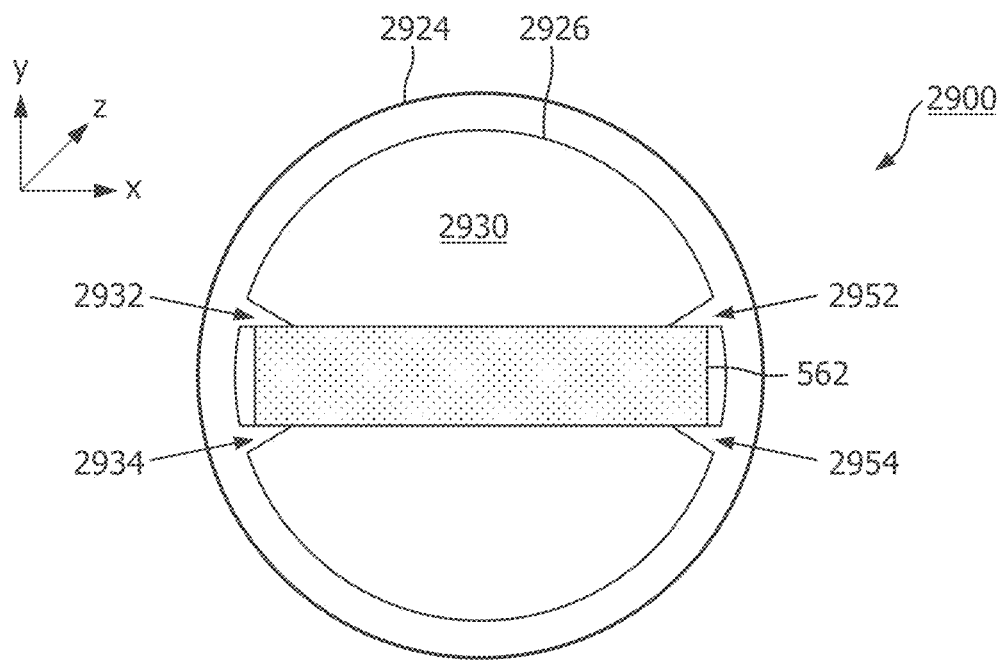
FIG. 30 is a back perspective view of a tip member with an imaging core in position according to embodiments of the present disclosure.

FIG. 30 is a back perspective view of the tip member 2900 with the imaging core 562 in position according to embodiments of the present disclosure. FIG. 30 illustrates the positioning of the imaging core 562 in the inner cavity 2930 viewing from the opened proximal end 2928 as shown by the line 2901. The imaging core 562 is encased within the inner cavity 2930 guided by the rails 2932, 2934, 2952, and 2954 along a first axis and a second axis about perpendicular to the first axis. In FIG. 28, the first axis is shown as the x-axis and the second axis is shown as the y-axis. The positioning of the imaging core 562 along the z-axis is restricted by the farthest distal end of the inner cavity 2930. The spaces between the inner cavity 2930 and the imaging core 562 are filled with similar encapsulating material as used for the inner cavity 1800 of the tip member 1700 and the inner cavity 2730 of the tip member 2700. The tip member 2900 can further include alignment members similar to the alignment members 1830 and 1832 to provide consistent alignment with the sleeve element 540, the crown element 520, and the flexible elongate member 108.

Figure 31:
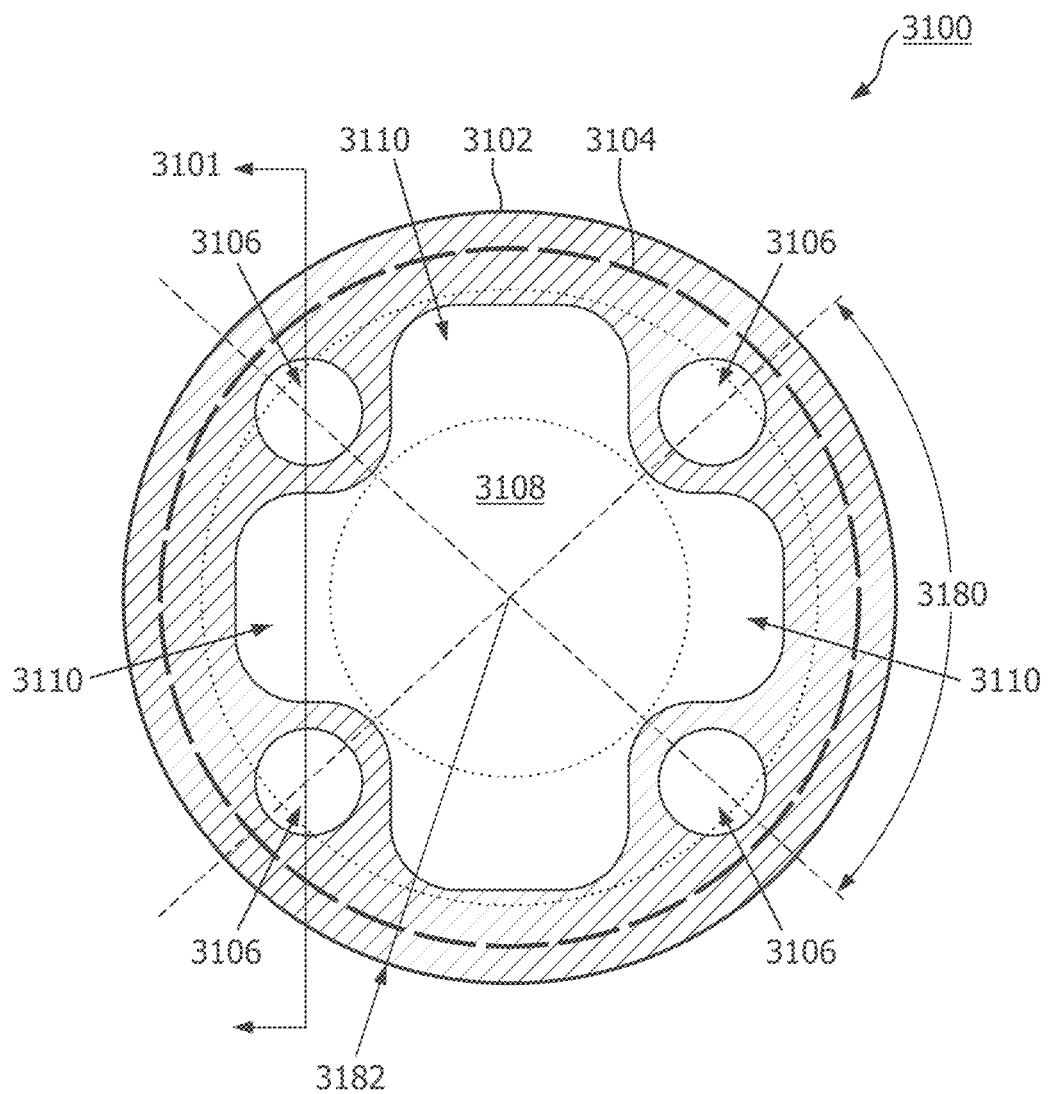
FIG. 31 is a cross-sectional view of a lined variable braided differential durometer multi-lumen catheter shaft according to embodiments of the present disclosure.
Figure 32:
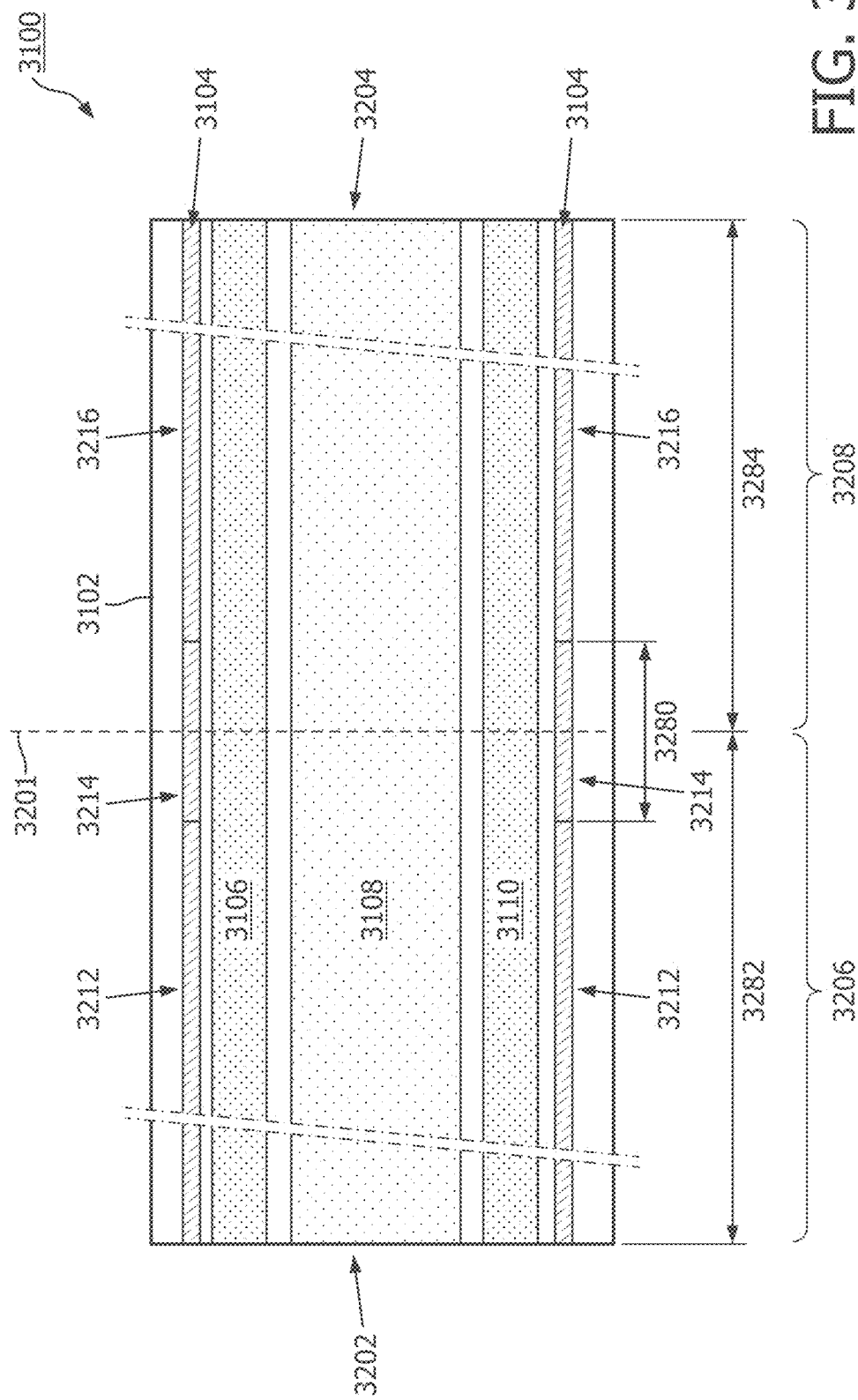
FIG. 32 is a cross-sectional longitudinal view of a lined variable braided differential durometer multi-lumen catheter shaft according to embodiments of the present disclosure.

FIGS. 31 and 32 illustrate a lined variable braided differential durometer multi-lumen catheter shaft 3100. The catheter shaft 3100 can be employed by the ICE device 110 in place of the flexible elongate member 108. FIG. 31 is a cross-sectional view of the lined variable braided differential durometer multi-lumen catheter shaft 3100 taken along a transverse axis of the catheter shaft 3100 according to embodiments of the present disclosure. FIG. 32 is a cross-sectional longitudinal view of the lined variable braided differential durometer multi-lumen catheter shaft 3100 taken along the line 3101 of FIG. 31 according to embodiments of the present disclosure. The catheter shaft 3100 has a distal end 3202 and a proximal end 3204. The catheter shaft 3100 is tubular in shape with a tubular wall 3102 and a primary lumen 3108. The primary lumen 3108 extends between the distal end 3202 and the proximal end 3204, for example, along a central longitudinal axis of the catheter shaft 3100.

The tubular wall 3102 is composed of a high durometer polymeric material at a distal segment 3206 and a low durometer polymeric material at a proximal segment 3208. For example, the high durometer polymeric material may have a durometer between 63D-80D and include materials such as Pebax® 72D or a suitable nylon. The low durometer polymeric material may have a durometer between 30D to 55D and include materials such as Pebax® 35D, Pebax® 45D, or a suitable nylon. The highly differing durometer of the tubular wall 3102 between the distal segment 3206 and the proximal segment 3208 creates a sharp transition or a high stiff-to-flex ratio in the catheter shaft 3100. Thus, the catheter shaft 3100 can be relatively rigid at the proximal segment 3208, but substantially pliable or flexible at the distal segment 3206. The steerability of the catheter shaft 3100, the amount of force to bend the catheter shaft 3100, and the locality of the bend force and/or actuations may depend on the durometer of the catheter shaft 3100. The sharp transition may improve the steerability, the amount of force, and/or the locality of the force when the catheter shaft 3100 is in use.

The catheter shaft 3100 further includes a plurality of secondary lumens 3106 extending longitudinally through a length of the tubular wall 3102. The primary lumen has a cross-shaped cross-sectional profile. This profile may be rounded (as shown in FIG. 31) or rectangular, for example. The secondary lumens 3106 are shaped and sized to accommodate pullwires such as the pullwires 507, 700, and 740. Thus, the secondary lumens 3106 are also referred to as pullwire lumens. The secondary lumens 3106 are positioned within the tubular wall 3102 radially spaced apart by an angle 3180 of about 90 degrees. The arms 3110 of the cross-shaped cross section form recesses that can anchor the angular positions of the secondary lumens 3106. For example, the secondary lumens 3106 are positioned between adjacent arms 3110 during manufacturing as described in greater detail herein. The primary lumen 3108 and the secondary lumens 3106 can be lined with a lubricious lining material (not shown) such as a polytetrafluoroethylene (PTFE) material. The lining material creates frictionless surfaces for threading, delivery, and actuations of pullwires or any other suitable diagnostic sensor assembly. In addition, the lining material can function as a support structure to prevent the primary lumen 3108 and the secondary lumens 3106 from collapsing. Further, the lining material can function as a barrier to protect abrasion caused by the frequent shifting or actuations of the pullwires and/or threading of the other diagnostic sensor assembly.

The catheter shaft 3100 further includes a braided layer 3104 embedded within the tubular wall 3102. The braided layer 3104 includes a distal portion 3212, a proximal portion 3216, and a transition portion 3214 between the distal portion 3212 and the proximal portion 3216. The braided layer 3104 can be composed of any suitable material and geometry. For example, the braided layer 3104 may include stainless steel flat wires, which may provide optimal usage of radial space and additional strength. The braided layer 3104 has braids with pitches that vary along a length of the tubular wall 3102. The braids can include any suitable braid pattern. The braid pattern may be selected to improve torque transmission (e.g., a 1:1 ratio from the proximal end 3204 to the distal end 3202), pushability, and/or kink resistance.

The braids at the distal portion 3212 are configured to have a higher per inch count (PIC) than the braids at the proximal portion 3216, for example, by about two times. The higher PIC at the distal portion 3212 provides a great flexibility to the distal segment 3206. The lower PIC at the proximal portion 3216 creates a stiffer support for the proximal segment 3208. For example, the distal portion 3212 has a first PIC, the proximal portion 3216 has a second PIC, and the transition portion 3214 has a varying PIC that varies smoothly from the first PIC to the second PIC. As shown, the distal portion 3212 of the braided layer 3104 is aligned to the distal segment 3206 of the catheter shaft 3100, the proximal portion 3216 of the braided layer 3104 is aligned to the proximal segment 3208 of the catheter shaft 3100, and the transition portion 3214 extends across a coupling point at which the low durometer distal segment 3206 meets the high durometer proximal segment 3208 as shown by the line 3201. The transition portion 3214 can extend a length 3280, for example, between about 5 mm to about 20 mm. The smooth varying braid pitches in the short transition portion 3214 can alleviate the weak kink point resulting from the abrupt transition between the low durometer distal segment 3206 and the high durometer proximal segment 3208.

Dimensions of the catheter shaft 3100 can vary in different embodiments. In some embodiments, the catheter shaft 3100 may be a 9 Fr catheter. Thus, the catheter shaft 3100 can have an outer diameter 3182 of about 3 mm. The distal segment 3206 can have a length 3282 between about 70 mm to about 81 mm. The length 3282 may vary based on a required bend radius for the catheter shaft 3100. The proximal segment 3208 can have a length 3282 between about 872 mm to 877 mm. The dimensions of the cross-shaped primary lumen 1308 can be sized to allow components (e.g., a printed circuit board (PCB) and/or a coaxial cable) to be thread through the lumen 1308 during assembly instead of using the coaxial cable as an anchor as in some configurations, and thus may improve handling responsiveness during operation. The low durometer material used in in the distal segment 3206 and the braided layer 3104 allows the catheter shaft 3100 to deflect up to a bend radius (e.g., the bend radius 305) of between about 13 mm to about 14 mm instead of about 27 mm to about 28 mm.

Figure 33:
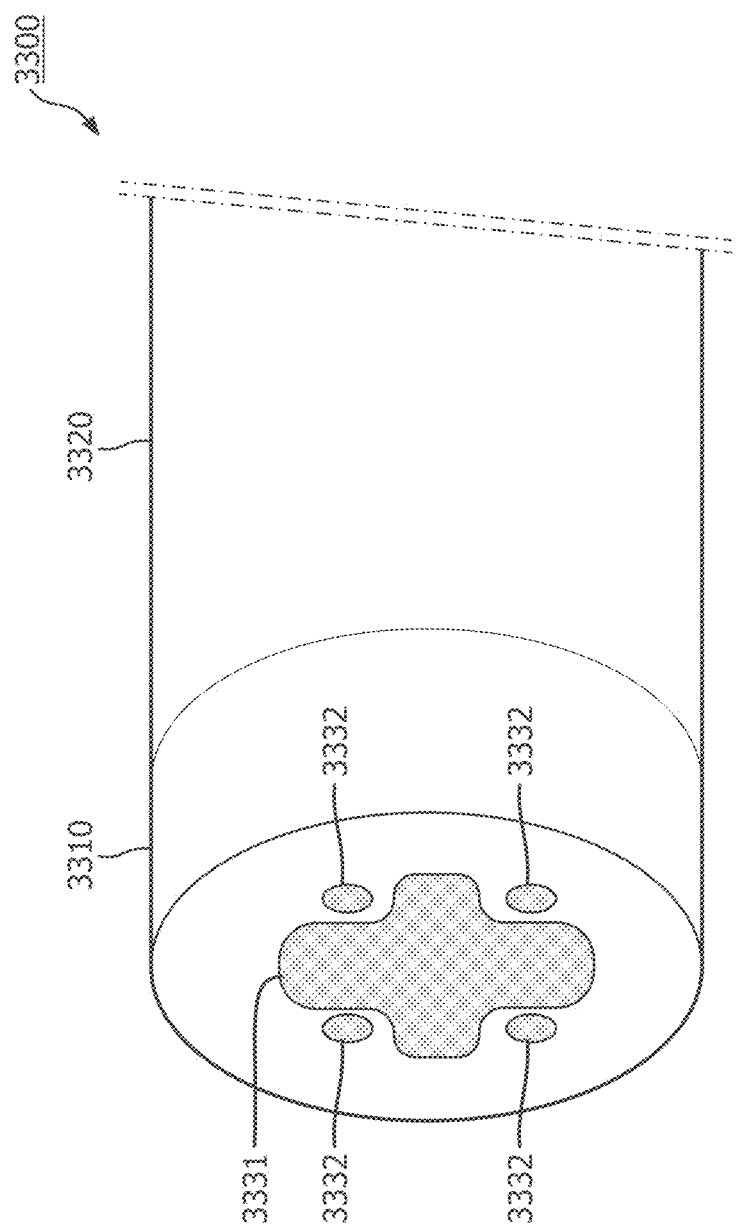
FIG. 33 is a perspective view of a multi-lumen inner extrusion in a stage of manufacturing according to embodiments of the present disclosure.

A method of manufacturing the catheter shaft 3100 is described with reference made to FIGS. 33-35. FIG. 33 is a perspective view of a multi-lumen inner extrusion 3300 in a stage of manufacturing according to embodiments of the present disclosure. The inner extrusion 3300 includes a high durometer proximal portion 3320 of a first material (e.g., Pebax® 72D) and a low durometer distal portion 3310 of a second material (e.g., Pebax® 35D or Pebax® 45D). The inner extrusion 3300 includes a primary lumen 3331 (e.g., primary lumen 3108) and a plurality of secondary lumens 3332 (e.g., secondary lumens 3106) extending between the high durometer proximal portion 3320 and the low durometer distal portion 3310.

Figure 34:
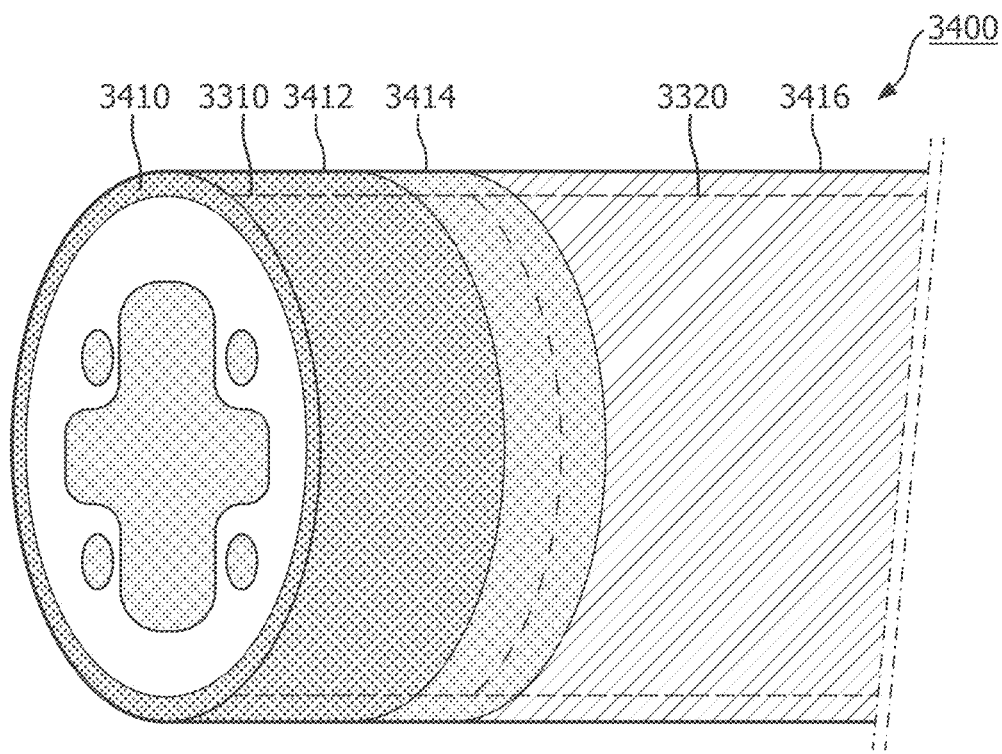
FIG. 34 is a perspective view of a braid reinforced inner extrusion in a stage of manufacturing according to embodiments of the present disclosure.

FIG. 34 is a perspective view of a braid reinforced inner extrusion 3400 in a stage of manufacturing according to embodiments of the present disclosure. As shown, a braided layer 3410 (e.g., the braided layer 3104) is formed over an outer surface of the inner extrusion 3300. The braided layer 3410 has a first braid portion 3416 (e.g., the proximal portion 3216) with a first braid pitch (e.g., with a first PIC) over the high durometer proximal portion 3320. The braided layer 3410 has a second braid portion 3412 (e.g., the distal portion 3212) with a second braid pitch (e.g., with a second PIC) over the low durometer distal portion 3310. The braided layer 3410 has a third braid portion 3414 (e.g., the transition portion 3214) with variable braid pitches (e.g., varying between the first PIC and the second PIC) across a transition between the high durometer proximal portion 3320 and the low durometer distal portion 3310.

Figure 35:
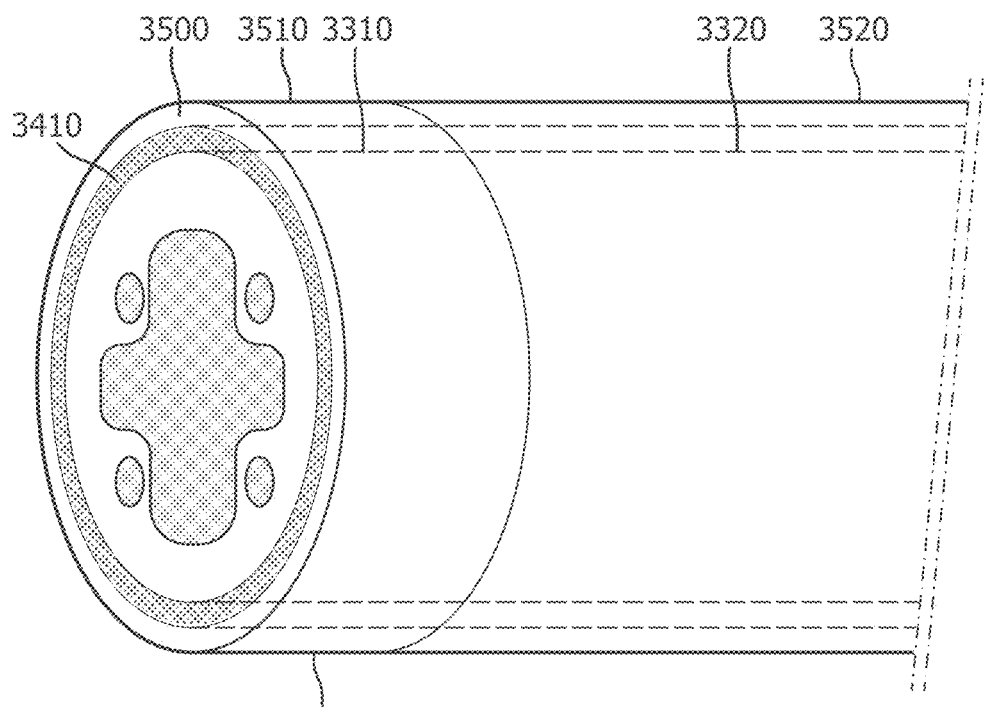
FIG. 35 is a perspective view of a single-lumen outer extrusion inserted over a braided inner extrusion in a stage of manufacturing according to embodiments of the present disclosure.

FIG. 35 is a perspective view of a single-lumen outer extrusion 3500 inserted over the braided inner extrusion 3400 in a stage of manufacturing according to embodiments of the present disclosure. The outer extrusion 3500 includes a high durometer proximal portion 3520 of a first material (e.g., Pebax® 72D) and a low durometer distal portion 3510 of a second material (e.g., Pebax® 35D or Pebax® 45D). The inner extrusion 3300 and the outer extrusion 3500 form the tubular wall 3102 of the catheter shaft 3100. The braided layer 3410 corresponds to the braided layer 3104 embedded within the tubular wall 3102.

After forming the catheter shaft 3100, pullwires such as the pullwires 700 and 740 may be thread through the secondary lumens 3106 according to predetermined orientations for providing the left, right, anterior, and posterior views. The distal end 3202 of the catheter shaft 3100 may be coupled to a tip assembly such as the tip assembly 102. For example, the coupling may include terminating or enclosing the braided element 3104 in a braid containment such as the braid containment 502. In addition, the coupling can include forming an interconnection as shown in FIG. 5. An electrical cable such as the electrical cable 566 connecting to the tip assembly may be threaded through the primary lumen 3108. The proximal end 3204 of the catheter shaft 3100 may be coupled to a steering control handle such as the handle 120.

The configuration of the lined variable braided differential durometer multi-lumen catheter shaft 3100 provides several benefits such as kink resistance, flexibility, high torquability, durability, and consistent alignment and articulations. The sharp transition between the low durometer distal segment 3206 and the high durometer proximal segment 3208 and the short transition portion 3214 of the braided element 3104 with varying PIC braids provide the kink resistance. The low durometer distal segment 3206, the high durometer proximal segment 3208, the high PIC braids at the distal portion 3212, and the low PIC braids at the proximal portion 3216 provide flexibility at the distal segment 3206 and rigid support at the proximal segment 3208. The cross-shaped cross-sectional profile of the primary lumen 3108 functions as an alignment agent to align the pullwire lumens or the secondary lumens 3106 such that pullwires such as the pullwires 507, 700, and 740 threaded through the secondary lumens 3106 can provide consistent articulation views under actuations. The primary lumen 3108 and the secondary lumens 3106 are lined with a lining material to provide frictionless surfaces, which may improve durability over multiple usages. Materials of the tubular wall 3102 and the braided element 3104 are selected to improve mechanical characteristics (e.g., the steerability of the catheter shaft 3100).

Any suitable material may be used for pullwires of the claimed invention. In certain instances, one or more pullwires are formed from a para aramid strands or filaments. The para aramid strands or filaments may be braided and then partially fused together (e.g. via thermal fusion) to form a wire. A particular para aramid wire can be formed at least partially from Kelvar®. The most common and reliable braided patterns of a construct of this size are the ones specified by the following military specs, A-A-55195/MIL-T-44100. The secondary finishing thermal fuse process helps increase its tensile strength but also its usability, preventing the individual strands from coming unwound during handling and threading.

The properties of para aramid enables several anchoring options on the distal end of the device at the point which the actuation force distribution (shaft compression point) ends (E.g. FIGS. 6A-6C). One option is a thermal fuse with an adjacent compatible polymeric material to allow the reflow of materials to encase its position. Another option is to use an additional component such as a washer or a ring to secure the wire's position and then reflow as you would the first option (e.g. FIG. 7). These options are available because of the heat resistant and high tensile properties of the para aramid wire.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus, comprising:
    an intracardiac echocardiography (ICE) catheter comprising:
        a catheter shaft comprising a proximal portion, a distal portion, and a cross-shaped lumen, wherein the cross-shaped lumen comprises a plurality of arms;
        an ultrasound transducer array positioned at the distal portion of the catheter shaft and configured to image a heart of a patient;
        an electrical cable coupled to the ultrasound transducer array and configured to carry signals associated with the ultrasound transducer array, wherein the electrical cable extends within the cross-shaped lumen; and
        a plurality of pullwires positioned outside the cross-shaped lumen and configured to deflect the distal portion of the catheter shaft, each of the plurality of pullwires positioned between a pair of adjacent arms of the plurality of arms of the cross-shaped lumen.

2. The apparatus of claim 1,
    wherein the catheter shaft comprises a plurality of pullwire lumens, each of the plurality of pullwire lumens positioned between a pair of adjacent arms of the plurality of arms of the cross-shaped lumen,
    wherein the plurality of pullwires is threaded through the plurality of pullwire lumens.

3. The apparatus of claim 2, wherein the plurality of pullwire lumens comprises four pullwire lumens.

4. The apparatus of claim 2, wherein the plurality of pullwire lumens is spaced from one another by 90 degrees.

5. The apparatus of claim 1, wherein the plurality of arms is arranged symmetrically.

6. The apparatus of claim 1, wherein the plurality of arms comprises four arms.

7. The apparatus of claim 1, wherein the catheter shaft further comprises a braided layer.

8. The apparatus of claim 7, wherein the braided layer surrounds the cross-shaped lumen and the plurality of pullwires.

9. The apparatus of claim 1,
    wherein the proximal portion of the catheter shaft comprises a first material,
    wherein the distal portion of the catheter shaft comprises a second material, and
    wherein a hardness of the first material comprises a first durometer and a hardness of the second material comprises a second durometer,
    wherein the second durometer is lower than the first durometer.

10. The apparatus of claim 8, wherein the cross-shaped lumen extends at least partially through the proximal portion and the distal portion.

11. The apparatus of claim 1, wherein the cross-shaped lumen is lined with a lubricious lining material.

* * * * *